US008348911B2

(12) United States Patent
Livacich et al.

(10) Patent No.: US 8,348,911 B2

(45) Date of Patent: Jan. 8, 2013

(54) EXTREME HEAT PROTECTION APPLIED DIRECTLY TO THE SKIN

(76) Inventors: John Livacich, Sunnyvale, CA (US); Kendyl A. Roman, Sunnyvale, CA (US)

( * ) Notice: Subject to any disclaimer, the term of this patent is extended or adjusted under 35 U.S.C. 154(b) by 473 days.

(21) Appl. No.: 12/381,630

(22) Filed: Mar. 12, 2009

(65) Prior Publication Data

US 2009/0229742 A1 Sep. 17, 2009

Related U.S. Application Data

(60) Provisional application No. 61/069,214, filed on Mar. 12, 2008.

(51) Int. Cl.
*A61F 7/00* (2006.01)

(52) U.S. Cl. ........................................................ 604/291

(58) Field of Classification Search ........... 604/289–291
See application file for complete search history.

(56) References Cited

U.S. PATENT DOCUMENTS

| | | | | |
|---|---|---|---|---|
| 4,169,169 | A * | 9/1979 | Kitabatake | 427/149 |
| 2005/0073644 | A1 * | 4/2005 | Markey, III | 351/44 |
| 2007/0036928 | A1 * | 2/2007 | Givens et al. | 428/40.1 |
| 2008/0035021 | A1 * | 2/2008 | Sambasivan et al. | 106/286.5 |

* cited by examiner

*Primary Examiner* — Melanie Hand

(57) ABSTRACT

Applicators provide heat shields for uncovered skin, in particular the face, hands, and other body parts that may not be clothed such as arms, legs, or torso. In one embodiment, a continuous heat shield is applied the entire face and ears. In another embodiment, a heat shield is applied to portions of the face and neck. In yet another embodiment, a heat shield is applied by multiple applicators. Sets of applicators apply a portion of a contiguous heat shield. Books contain multiple sets of applicators. Camouflage is used for military concealment. Other uses include firefighting, iron working, glass blowing and cooking. Entrained ceramic particles provide heat reflection and insulation.

20 Claims, 20 Drawing Sheets

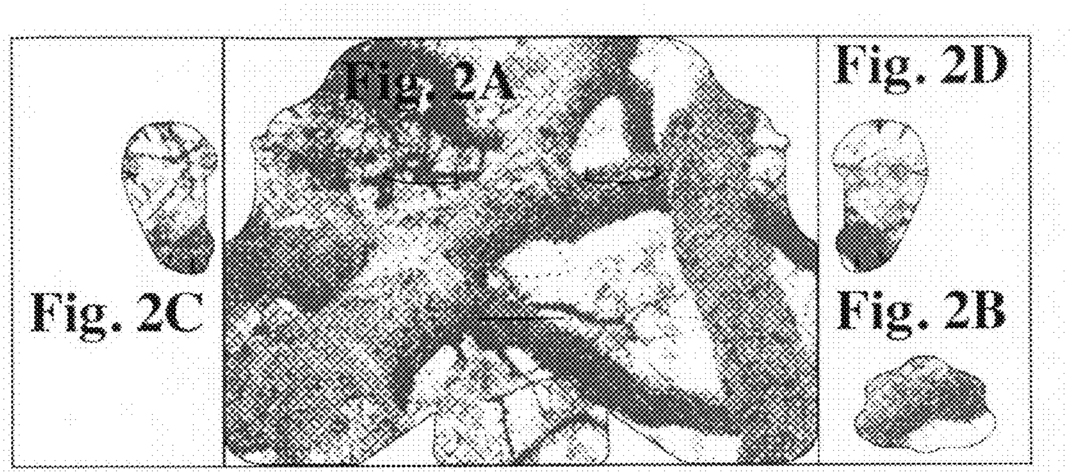
Fig. 2
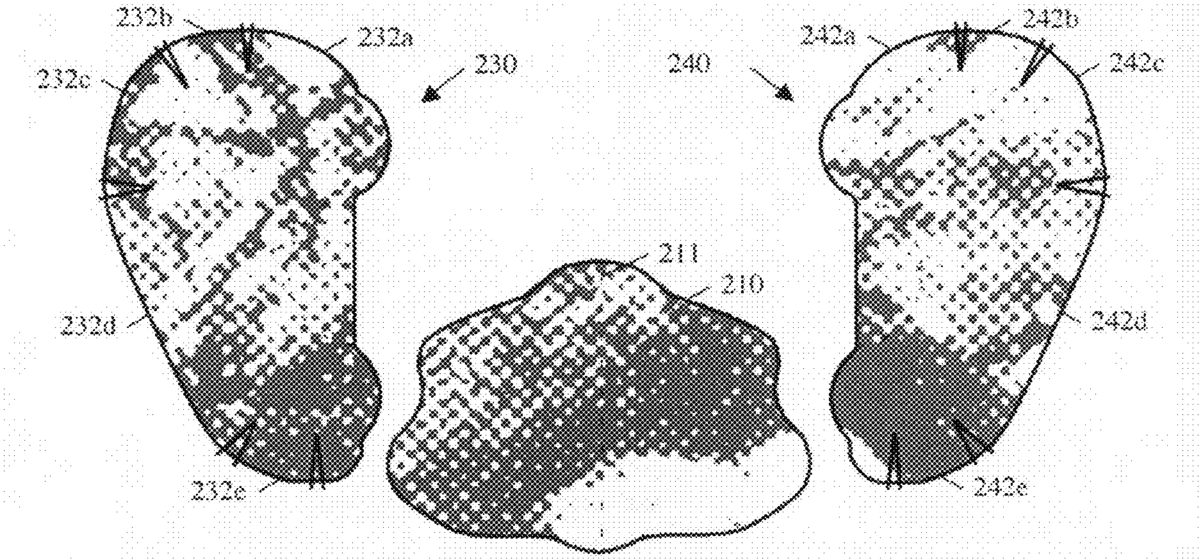
Fig. 2C
Fig. 2D
Fig. 2B

EXTREME HEAT PROTECTION APPLIED DIRECTLY TO THE SKIN

RELATED APPLICATIONS

This application claims priority under 35 U.S.C. §199(e) of the co-pending U.S. provisional application Ser. No. 61/069,214, filed Mar. 12, 2008, entitled "Face, Hand, and Skin Camouflage".

BACKGROUND

1. Field of the Invention

This invention relates to heat shields applied directly to uncovered skin, in particular the face, hands, and other body parts that may not be clothed such as arms, legs, or torso.

2. Overview

There is a need for hunters and soldiers to completely camouflage themselves to avoid detection. Both hunters and soldiers have successfully used camouflaged clothing and hats to camouflage most of their bodies and their equipment; however, for various reasons it is not practical to cover the face, which contains the eyes, ears, nose, and mouth, or sometimes the hands, arms, legs, and torso. The lack of comfortable, practical camouflage for the uncovered skin such as the face, ears, hands, and so forth results in unwanted detection by prey or enemies.

There is a need for hunters, soldiers, actors, sports fanatics, and costume wearers to apply one of many predetermined color patterns to their skin, in particular, their face, hands and other body parts that may not be clothed such as arms, legs, or torso. There is also a need for makers of camouflage patterns to create market awareness for their particular patterns.

There is a need for soldiers, firemen, glass blowers, metal workers, and others in occupations that are at high risk of fire, bombs and other high heat issues to wear heat protective clothing. Soldiers, for example, must wear special heat protective clothing while in the field outside of the safe areas because they are exposed to improvised explosive devices (IEDs) as roadside bombs that can reach temperatures of up to several thousand degrees Fahrenheit.

3. Prior Art

Development of camouflage patterns, especially in the hunting market has become a relatively large and competitive business. Various brands of camouflage designs such as Mossy Oak, Real Tree, and Predator, compete to have their camouflage patterns adopted for use in hunting clothing and equipment.

Different methods and devices have been developed in an attempt to camouflage uncovered skin. These include the use of face paint, or makeup, and fabric masks, or netting.

Face paint may come in the form of small bottles, tubes, or sticks. Makeup kits with multiple partitions and two sided sticks are commonly used to provide two or more camouflage colors. However the design must be drawn from scratch by hand, usually by the wearer on the wearer's own face. Face paint and makeup have several disadvantages, including being odorous, greasy, heavy, hot, sticky, messy, imprecise, time-consuming to apply and remove, and difficult to remove. When hunting, scent is a major concern because prey can detect the odor from the face paint. Face paint and makeup is messy and can damage expensive clothing or equipment. Because it is greasy, heavy, hot and sticky it is uncomfortable to wear. It is difficult to apply and imprecise in its results.

Face concealment devices include various fabric masks, buffs, neck sleeves, and camouflaged netting designed to hang from a hat or wrap around the head. Conventional face concealment devices have several disadvantages, including being heavy, hot, obstructive, disruptive, and expensive. A fabric mask for example may block a hunter's vision, catch on branches, or disrupt the movement of a bow string. A thick fabric covering the ears distorts the hearing of the wearer.

More recently, some have attempted to apply camouflage to various portions of the face with pieces of vinyl with reusable adhesive. These have several disadvantages including being uncomfortable, non-breathable, hot, obstructive and disruptive.

Although they have not been used previously as skin camouflage, temporary tattoos are used in a different field for other purposes. Temporary tattoos typically contain small images such as a miniature flag or a small butterfly. A temporary tattoo is made by printing one or more small images on a special backing paper or film that is processed with multiple layers of coating. See U.S. Pat. No. 4,169,169. Typically, the first layer applied to the backing is a sizing agent, the second layer is a non-stick silicon release coating, and the third layer is a transfer film composed of gelatin or other polymeric material. The pigments are printed on the transfer film. With a decal-style temporary tattoo, the paper is moistened to release the transfer film, which may be applied to the skin.

Temporary tattoos are conventionally applied to relatively flat, small areas on the cheeks, arms, legs, or back, but have not been used to cover large, uneven surfaces of the body such as the entire face or hands and fingers.

More recently waterless tattoos have been developed which place the pigment in a translucent adhesive substrate. See U.S. Pat. No. 4,594,276. The adhesive substrate has peel off paper on one side which when removed allows the adhesive side to be attached to the skin. The backing can be plastic film that is removed after the adhesive substrate has been pressed on the skin.

What is needed is a means of applying one of many predetermined camouflaged patterns to uncovered skin, in particular the face, hands, and other body parts that may not be clothed such as arms, legs, or torso, without being, odorous, greasy, heavy, hot, sticky, messy, imprecise, time-consuming to apply and remove, difficult to remove, obstructive, disruptive, or expensive.

What is needed is a means of applying skin heat protection that is flexible, breathable, sweat-through, and comfortable to uncovered skin, in particular the face, hands, and other body parts that may not be clothed such as arms, legs, or torso, without being, odorous, greasy, heavy, hot, sticky, messy, imprecise, time-consuming to apply and remove, difficult to remove, obstructive, disruptive, or expensive.

SUMMARY OF THE INVENTION

Accordingly, it is an objective of the present invention to provide a new use of temporary tattoo devices and process to apply one of many predetermined camouflaged patterns to uncovered skin, in particular the face, hands, and other body parts that may not be clothed such as arms, legs, or torso.

OBJECTS AND ADVANTAGES

Accordingly, beside the objects and advantages described above, some additional objects and advantages of the present invention are:

1. To provide a comfortable and practical means of camouflaging a face.
2. To provide a comfortable and practical means of camouflaging a hand.

3. To provide a comfortable and practical means of camouflaging unclothed body parts.
4. To provide a more precise means of applying a predetermined pattern over a large area of human skin.
5. To provide a more efficient method of applying a predetermined pattern over a large area of human skin.
6. To provide a method of matching skin camouflage with the wearer's apparel.
7. To provide a method of applying a continuous pattern across the apparel and uncovered skin of a wearer.
8. To provide a method of creating a camouflage pattern from a plurality of camouflage elements such as leaves and branches.
9. To provide a method of applying precise, efficient, and consistent face or body makeup for a stage actor.
10. To provide a method of applying precise, efficient, and consistent face or body makeup for a video actor.
11. To provide a method of applying precise, efficient, and consistent face or body design for a costume.
12. To provide a method of applying precise, efficient, and consistent face or body design for a sports fanatic.
13. To provide a method of applying precise, efficient, and uniform face or body design for a member of a group, such as one participating a parade, protest, wedding or fund-raiser.
14. To provide a skin camouflage that is easy to carry, apply, and remove.
15. To provide a skin camouflage with a long shelf life (storage period).
16. To provide a set of skin camouflage applicators having a matching camouflage pattern.
17. To provide a book of multiple sets of a single camouflage pattern.
18. To provide a book of multiple camouflage patterns, each in a set.
19. To provide a fascinating and effective tradeshow demonstration of a particular brand of camouflage pattern.
20. To provide a consistent pattern to be used by a military unit for a predetermined period of time.
21. To provide a method of applying long lasting sunburn protection for hunters, soldiers, and other outdoorsmen, athletes, and fans.
22. To provide a method of applying heat protection for firemen, soldiers, and others who are in the proximity of fire, bombs, etc.

DRAWING FIGURES

In the drawings, closely related figures have the same number but different alphabetic suffixes.

FIGS. 2A through 2D illustrate various applicators that apply a pattern to the entire face including eyelids, lips; ears and nose.

REFERENCE NUMERALS IN DRAWINGS

Figure 1:
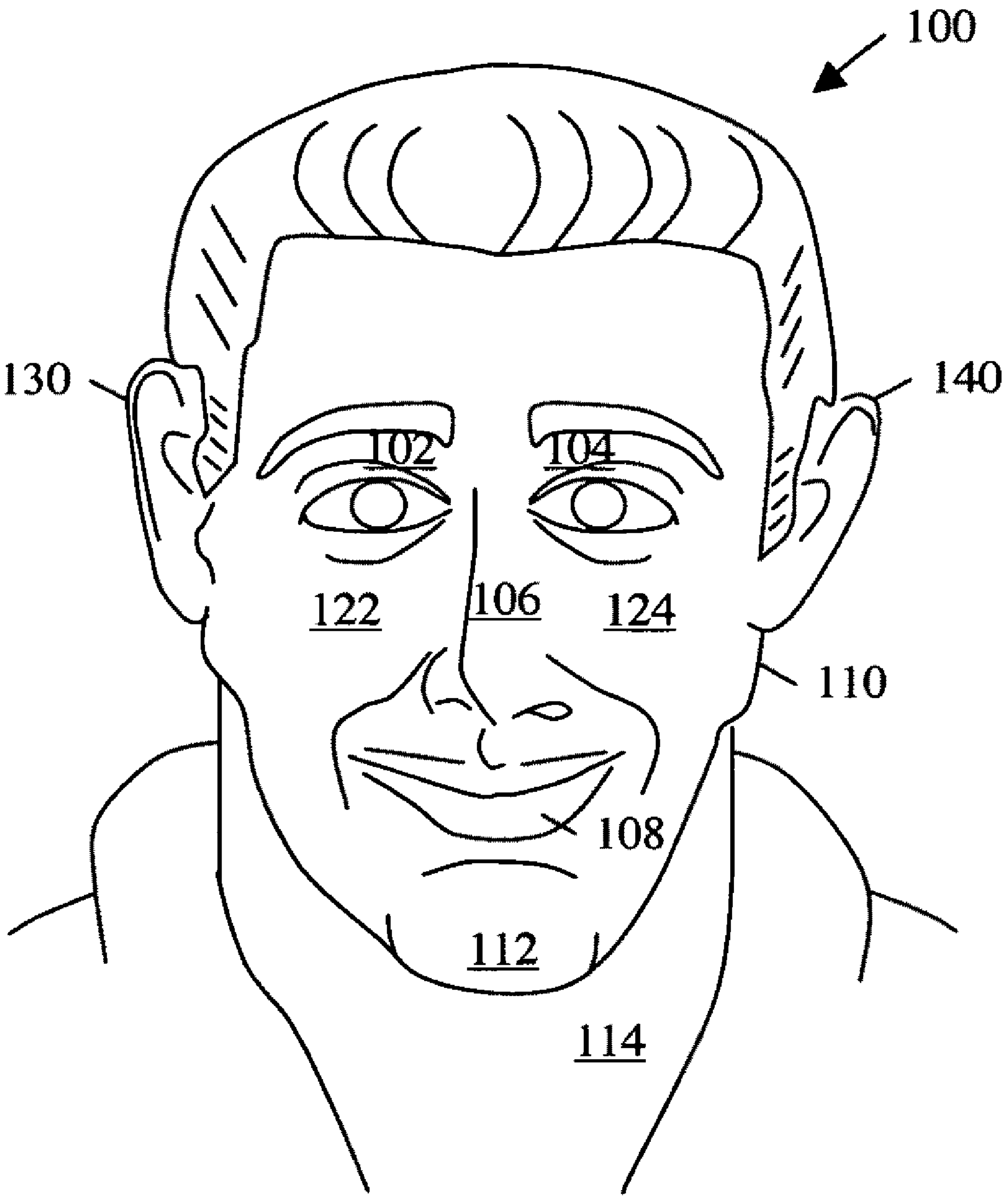
FIG. 1 shows a user.

| | |
|---|---|
| 100 | user |
| 102 | first eyelid |
| 104 | second eyelid |
| 106 | nose |
| 108 | lips |
| 110 | face |
| 112 | chin |
| 114 | neck |
| 122 | first cheek |
| 124 | second cheek |
| 130 | first ear |
| 140 | second ear |
| 200 | face applicator |
| 202 | first eyelid tab |
| 204 | second eyelid tab |
| 206 | nose cutout |
| 208 | lip cutout |
| 210 | nose applicator |
| 211 | nose fold |
| 212 | first chin dart |
| 214 | second chin dart |
| 216 | first hairline |
| 218 | second hairline |
| 222 | first ear marker |
| 224 | second ear marker |
| 230 | first ear applicator |
| 232 (a-f) | first ear tabs |
| 240 | second ear applicator |
| 242 (a-f) | second ear tabs |
| 250 | wide nose applicator |
| 300 | user showing arms |
| 302 | hand |
| 304 | forearm |
| 306 | upper-arm |
| 310 | hand applicator |
| 320 (a-b) | forearm applicator |
| 330 (a-b) | upper-arm applicator |
| 332 (a-i) | hand applicator section |
| 340 | alternate hand applicator |
| 342 | palm applicator |
| 344 | index finger applicator |
| 346 | middle finger applicator |
| 348 | ring finger applicator |
| 350 | pinky finger applicator |
| 352 (a-d) | finger applicator alignment points |
| 354 (a-i) | palm applicator section |
| 400 | hunting pattern |
| 410 | military pattern |
| 500 | pattern continuity |
| 550 | coat/jacket |
| 560 | hat/hood |
| 600 | first half-face applicator |
| 602 | second half-face applicator |
| 606 (a-b) | half nose cutout |
| 608 (a-b) | half mouth cutout |

-continued

| | |
|---|---|
| 612 | first chin dart |
| 614 | second chin dart |
| 620 | neck applicator |
| 640 | alternate half-face applicator |
| 642 | second alternate half-face applicator |
| 650 | first half-brow applicator |
| 652 | second half-brow applicator |
| 654 (a-b) | eyelid cutout |
| 800 (a-c) | applicator set |
| 801 | nose page |
| 810 | front matter |
| 820 | book |
| 830 | book container |
| 910 (a-b) | leaf element |
| 920 (a-b) | branch element |
| 1004 | dry release layer |
| 1006 | film layer |
| 1008 | pigment layer |
| 1010 | adhesive layer |
| 1012 | peel off layer |
| 1014 | wet release layer |
| 1016 | solute layer |
| 1018 | opaque layer |
| 1020 | heat shield layer |
| 1022 | ceramic bubbles |
| 1024 | adhesive/heat shield layer |

SPECIAL DEFINITIONS face—human surface tissue between the ears and between the hairline, and the bottom of the jaw, including the eyelids, nose, and lips.

applicator—a device for applying a predetermined pattern of pigments to human skin.

DESCRIPTION OF THE INVENTION

The present invention comprises a plurality of applicators that collectively apply a predetermined pattern to a relative large area of uncovered skin, such as the face, hands, and other body parts that may not be clothed such as arms, legs, or torso.

In a preferred embodiment, the applicators apply a predetermined pattern of pigments to human skin. The predetermined pattern may be any one of a plurality of camouflage patterns. A number of patterns are available with high resolution printing.

FIG. 1—User

FIG. 1 shows a user 100. The user 100 has a face 110 including eyelids (102, 104), nose 106, lips 108, chin 112, and cheeks (122, 124). The neck 114 and ears (130, 140).

If the user 100 is a hunter or soldier, uncovered portions of the body, such as the face 110, neck 114, ears (130, 140), and hands 302 (FIG. 3B) are easily detected by prey or enemies. These parts of the body are constantly moving (which is part of the reason they are more comfortably left uncovered) making unwanted detection even more of a problem.

FIGS. 2A Through 2D—Skin Camouflage Applicators

Figure 2A:
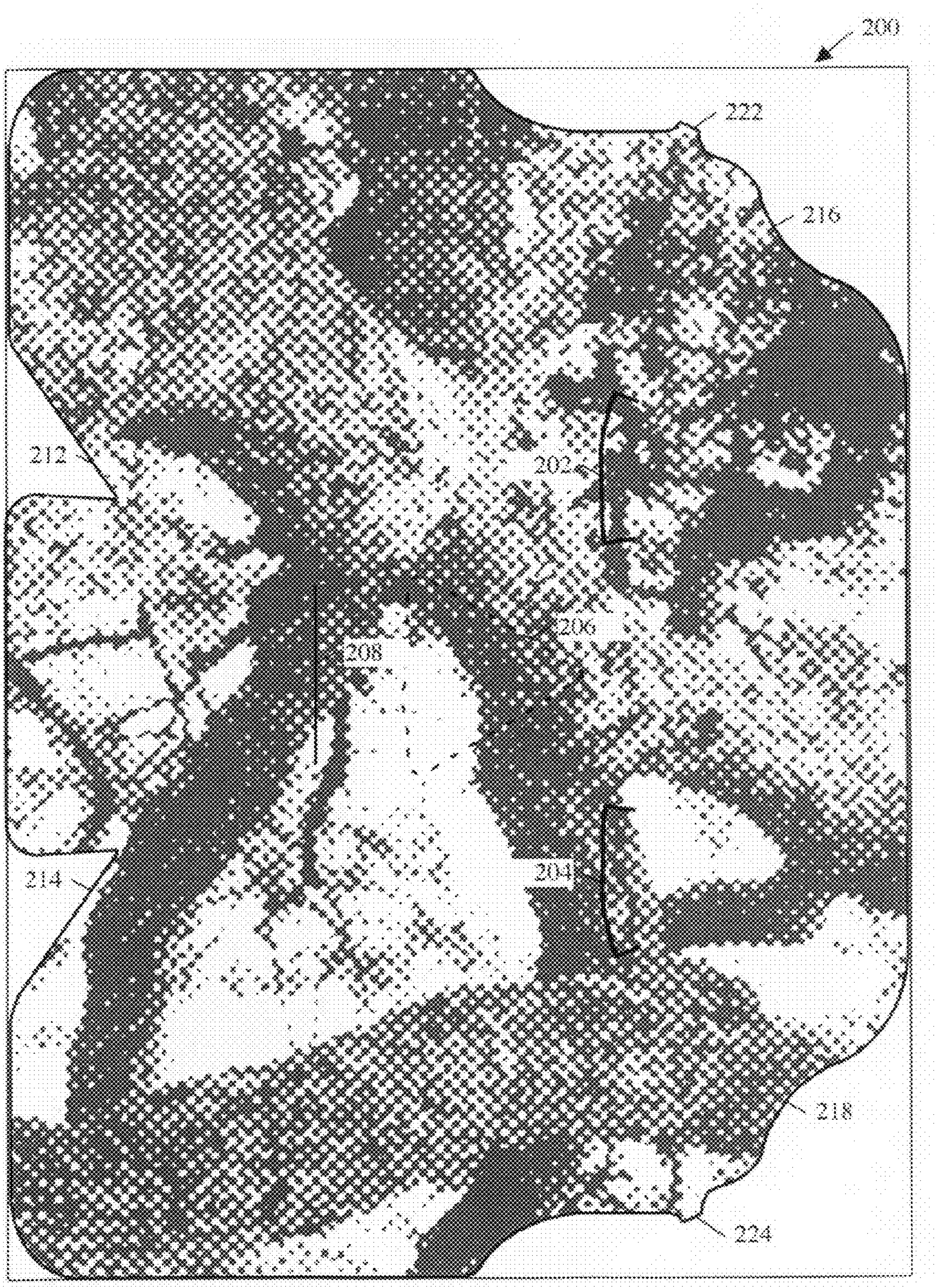

FIG. 2 shows an arrangement of FIGS. 2A through 2D, which illustrate various applicators that apply a pattern to the entire face 110 including eyelids (102, 104), nose 106, lips 108, chin 112, and checks (122, 124), and ears (130, 140).

FIG. 2A illustrates a face applicator 200 comprising eyelid tabs (202, 204), nose cutout 206, lip cutout 208, chin darts (212, 214). Face applicator 200 features curves along the hairlines on each side (216, 218, respectively). Optionally, the face applicator 200 comprises ear markers (222, 224) that help align the applicator on the face 110.

The eyelid tabs (202, 204) allow the user to more accurately apply the pattern to the eyelids (102, 104, respectively). The eyelid tabs (202, 204) also allow the user to see through the applicator when using a mirror to self apply the pattern.

The nose cutout 206 allows the rest of the face applicator 200 to pass over the nose and lie more smoothly along the skin. The nose cutout 206 also helps the user align the pattern to the face 110 using the nose 106 as a central anchor point. The lip cutout 208 allows the pattern to be applied to the lips. Both the nose cutout 206 and the lip cutout 208 allow the user to breath while applying the sheet to the face 110.

The chin darts (212, 214) allow the face applicator 200 to fold under around the chin 112 and along the jaw. The darts (212, 214) allow the face applicator 200 to form a 3-dimensional shape (see FIG. 3A).

FIG. 2B illustrates a nose applicator 210 having a nose fold 211. The pattern on the nose applicator 210 is shown matching the missing portion from the nose cutout 206. The pattern may be skewed (as shown) on the nose applicator 210 so that when applied to the 3-dimensional face 110 and nose 106, the pattern appears the same. In this example, a branch passes diagonally across the face applicator 200 and one side of the nose applicator 210 has bark matching that portion of the branch. This is an example of an aspect of the invention where a continuous pattern is applied using more than one applicator.

FIGS. 2C and 2E illustrate respective ear applicators (230, 240). As shown in this illustration (e.g. FIG. 2), the pattern on the respective ear applicators (230, 240) matches the overall pattern of the face applicator 200. The ear markers (222, 224) aid the user in aligning the ear applicators with the pattern applied by the face.

The ear applicators (230, 240) each comprises ear tabs (232*a* through 232*f*, and 242*a* through 242*f*, respectively), which allow the ear applicators (230, 240) to apply the pattern to the top and back of the ears (130, 140) and allow the ear applicators (230, 240) to fit different size ears.

Another aspect of the invention is that the pigment and transfer substrate can contain UV sunburn protection. The nose 106 and tops of the ears (130, 140) are typically more susceptible to sunburn.

Figure 3A:
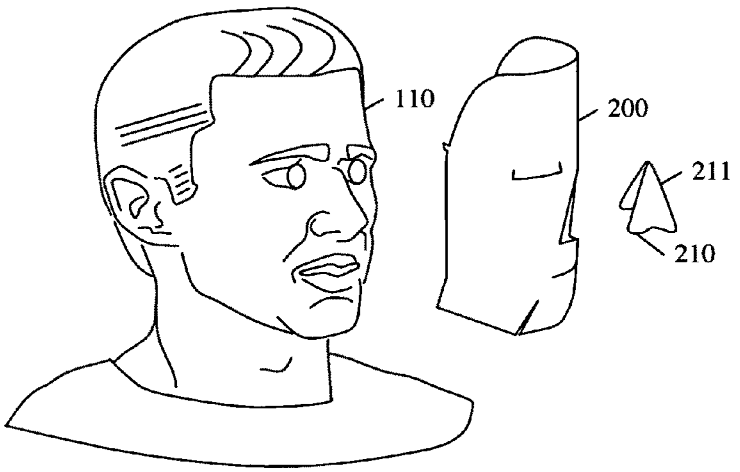
FIG. 3A illustrates the application of a pattern to the face and nose.

FIG. 3A—Skin Camouflage Applied to the Face

FIG. 3A illustrates the application of a pattern to the face 110 and nose 106 using a two applicators. The nose applicator 210 is cut from a flat sheet and folded at the nose fold 211. The face applicator 200 is cut from another flat sheet, with the various darts (e.g. skin darts 212 and 214), eyelid tabs (202, 204), nose cutout 206, and lip cutout 208. The 3-dimensional shape can be held, for example, by taping the darts closed. The face applicator 200 is then aligned over the nose 106 and pressed into place. The eyelid tabs (202, 204) are pressed on each respective eyelid (102, 104). The pattern is applied to the lips 108 using lip cutout 208 for added flexibility.

The ear applicators (230, 240) are next aligned to the face pattern and applied to the respective ears (not shown in FIG. 3A).

Figure 3B:
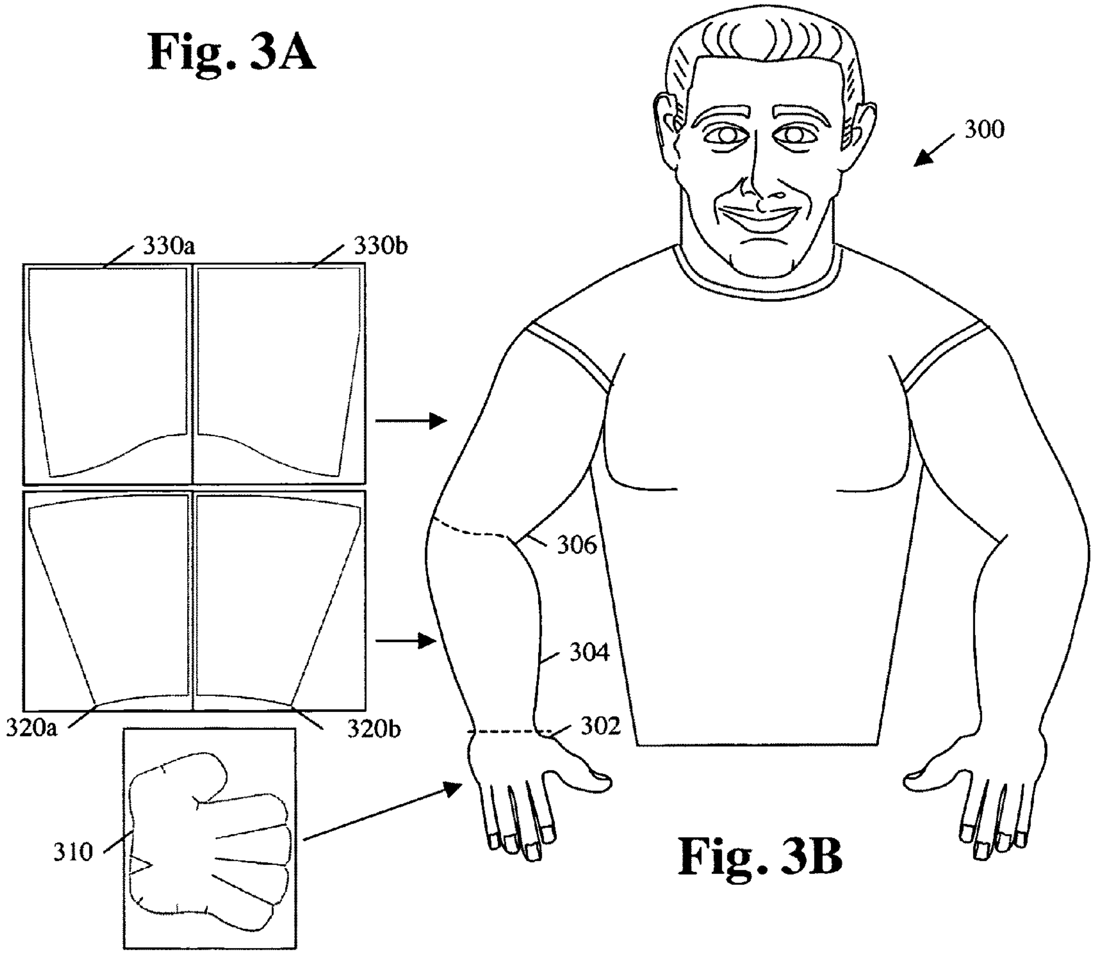
FIGS. 3B through 3D illustrate applicators for applying a pattern to the hand, forearm, and upper-arm.
Figure 3C:
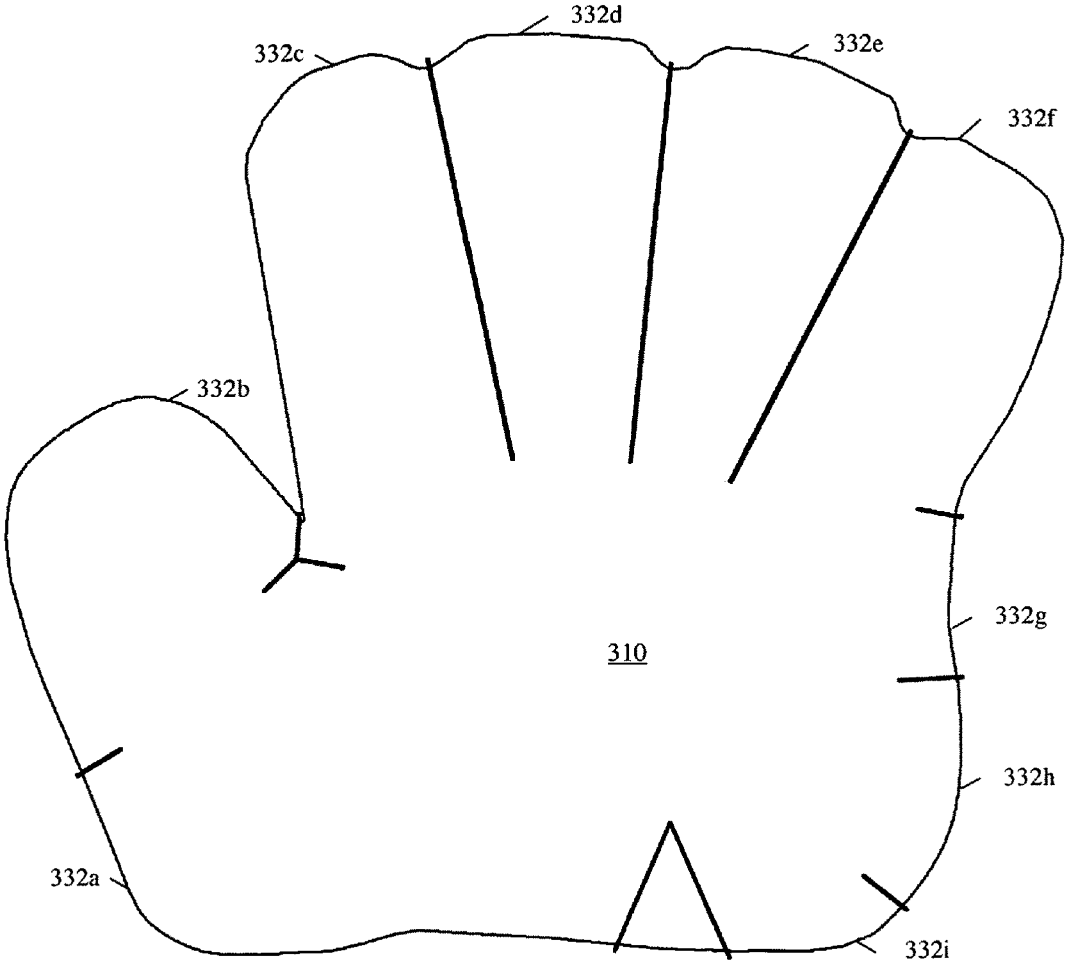
Figure 3D:
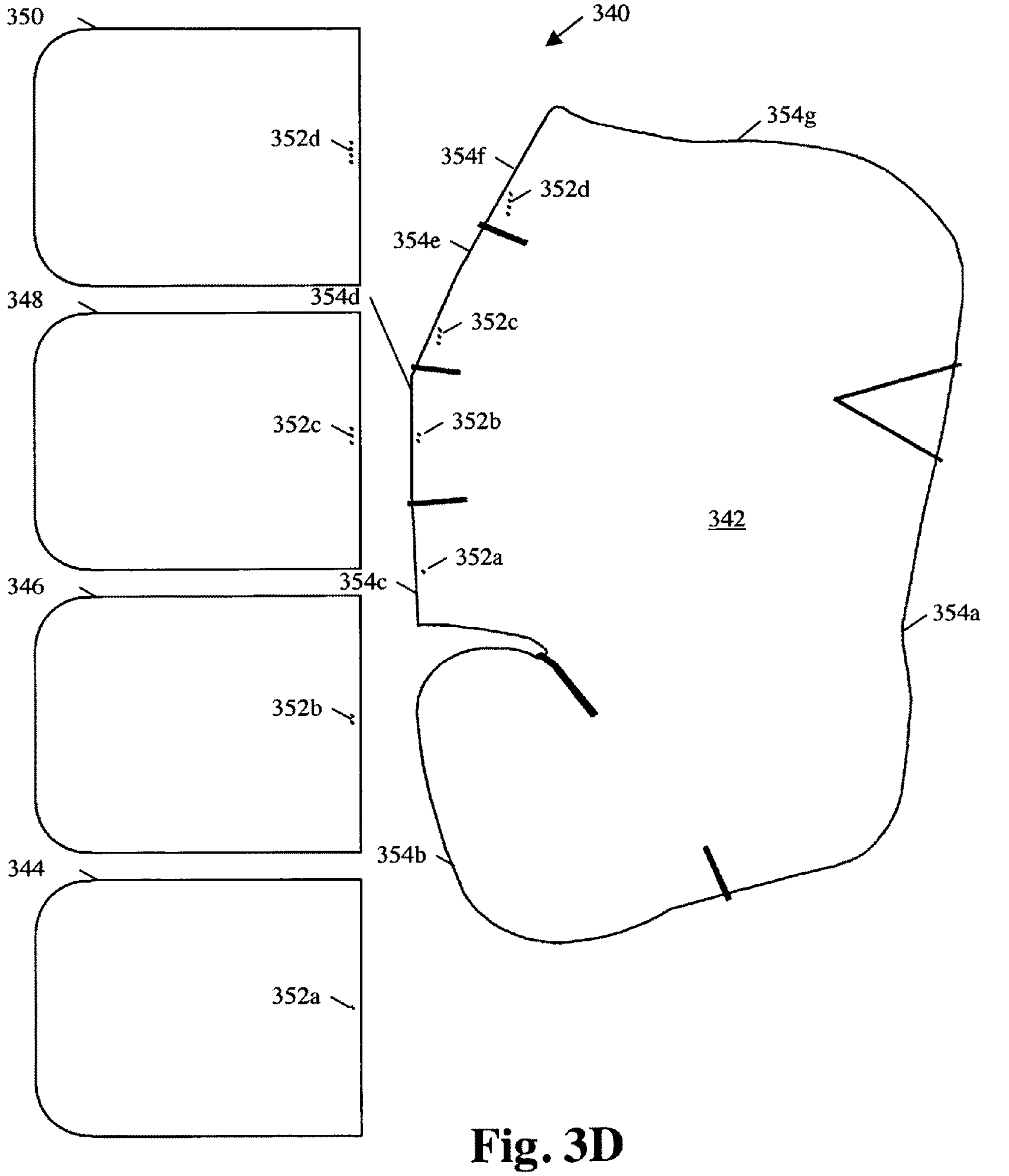

FIGS. 3B Through 3D—Skin Camouflage Applied to the Hand and Arm

FIG. 3B illustrates applicators for applying a pattern to the hand 302, forearm 304, and upper-arm 306. The user 300 is shown with arms and torso. The arm is shown comprising the hand 302, the forearm 304, and the upper-arm 306. In this embodiment, the set of applicators includes a hand applicator 310, forearm applicators 320 (shown as two separate sheets

320*a* and 320*b*, respectively), and upper-arm applicators 330 (shown as two separate sheets 330*a* and 330*b*, respectively).

FIG. 3C shows the hand applicator 310 comprising various hand applicator sections 332 (*a-i*) and darts so that the desired pattern is applied to the 3-dimensional surface of the hand with its thumb and fingers.

FIG. 3D shows an alternate hand applicator 340 comprising a palm applicator 342 which includes the thumb and 4 separate finger applicators: index finger applicator 344, middle finger applicator 346, ring finger applicator 348, pinky finger applicator 350. The palm applicator 342 comprises various palm applicator sections 354(*a-i*) and darts so that the desired pattern is applied to the 3-dimensional surface of the hand with its thumb. Each finger applicator is applied to the palm applicator 340 at finger applicator alignment points 352 (*a-d*). Each corresponding finger applicator attaches to the corresponding finger applicator alignment point on the palm applicator 340. More specifically, the index finger applicator 344 is aligned at finger applicator alignment points 352*a*, middle finger applicator 346 is aligned at finger applicator alignment points 352*b*, ring finger applicator 348 is aligned at finger applicator alignment points 352*c*, and pinky finger applicator 350 is aligned at finger applicator alignment points 352*d*.

Preferable the various applicators in a pattern set 800 are comprised of standard sized sheets, such as, for example, 8½x11 inch sheets.

FIG. 4—Multiple Patterns

Figure 4A:
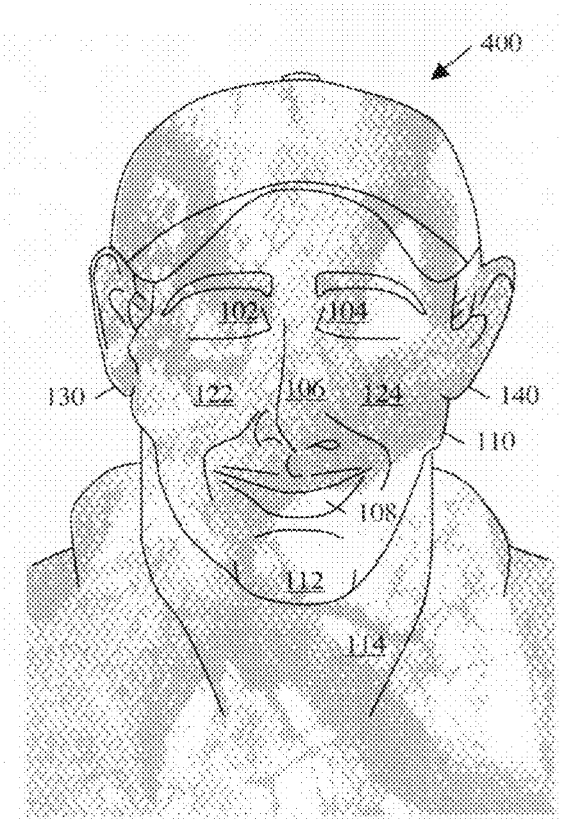
FIGS. 4A and 4B show the use of the application of multiple patterns which match the users apparel.
Figure 4B:
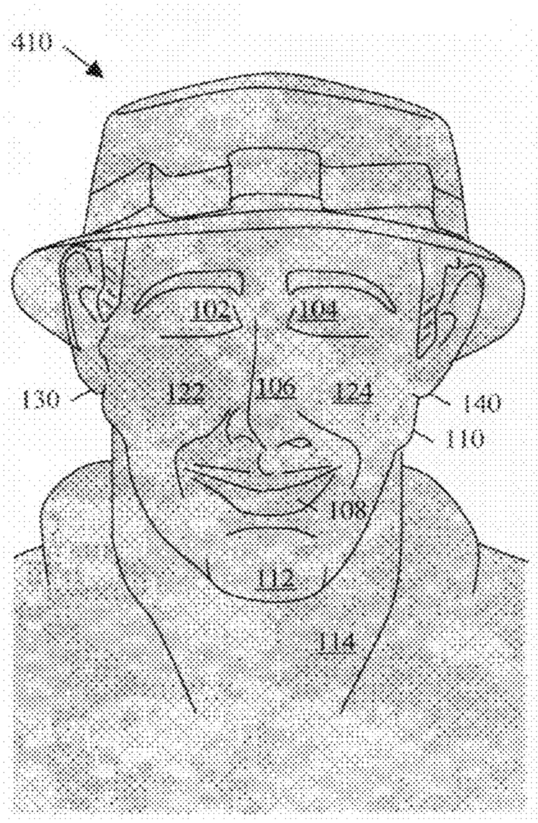

FIGS. 4A and 4B show the use of the application of multiple patterns which match the users apparel. FIG. 4A shows the user after applying a hunting pattern 400 that matches his hunting apparel. In contrast, FIG. 4B shows the user after applying a military pattern 410 that matches his military apparel.

There are many different camouflage patterns. For example, for the hunting pattern 400, one company Mossy Oak, for example, has Break-Up®, Treestand®, Duck Blind®, Brush®, and Obsession®. Other companies provide other patterns. The military pattern 410 could be the tradition military camouflage, the new Universal Camouflage Pattern used by the U.S. Army, or military camouflage for snow, desert, or night operations.

An aspect of the current invention is having a set 800 of applicators for each different camouflage pattern.

Figure 5:
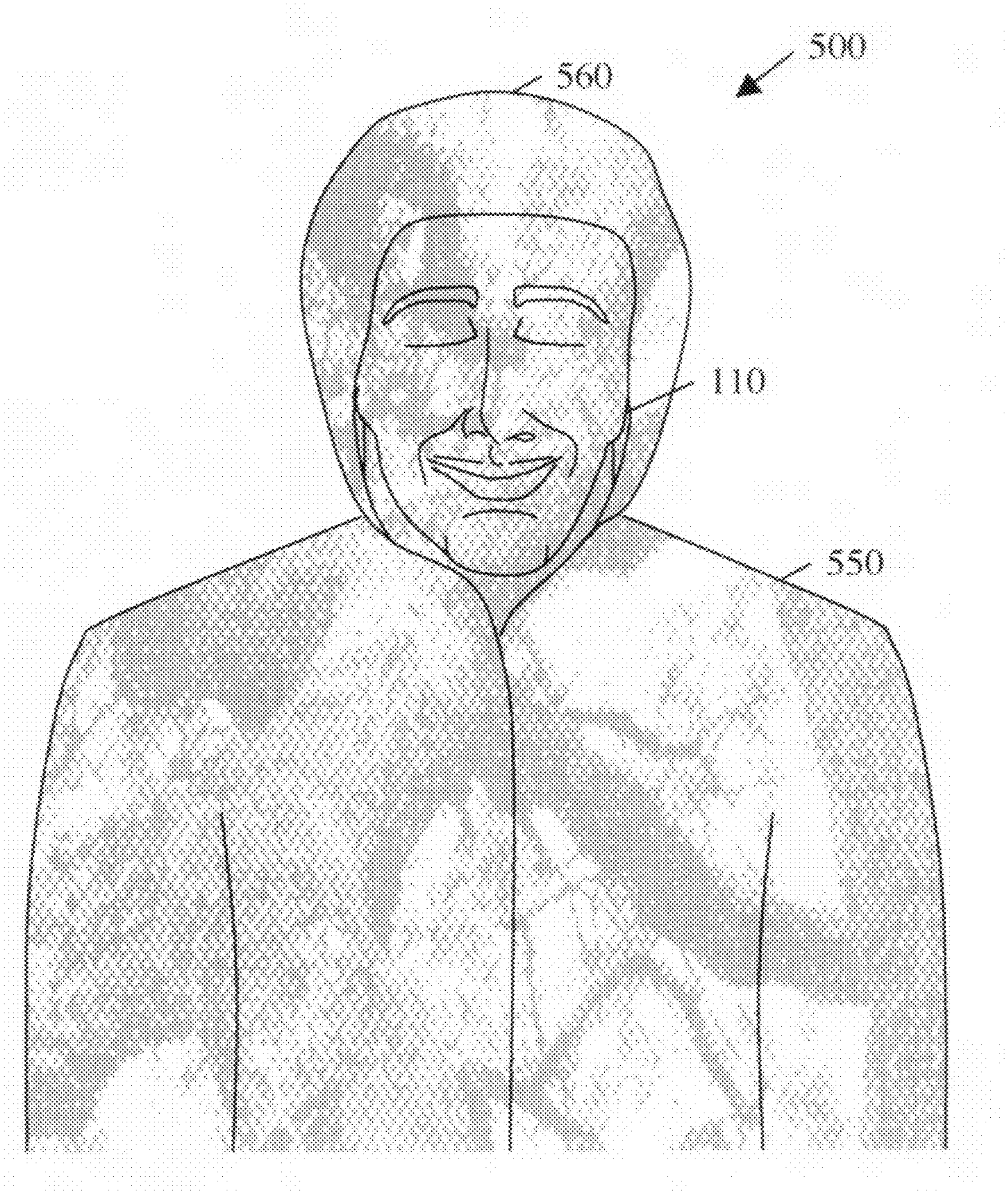
FIG. 5 shows a continuous pattern applied to jacket, face, and hood.

FIG. 5—Continuous Pattern Across Skin and Apparel

FIG. 5 shows pattern continuity 500 where a continuous pattern applied to jacket 550, face 110, and hood 560. An aspect of the invention is that a continuous pattern is applied to the uncovered skin which matches the apparel being worn.

Figure 6:
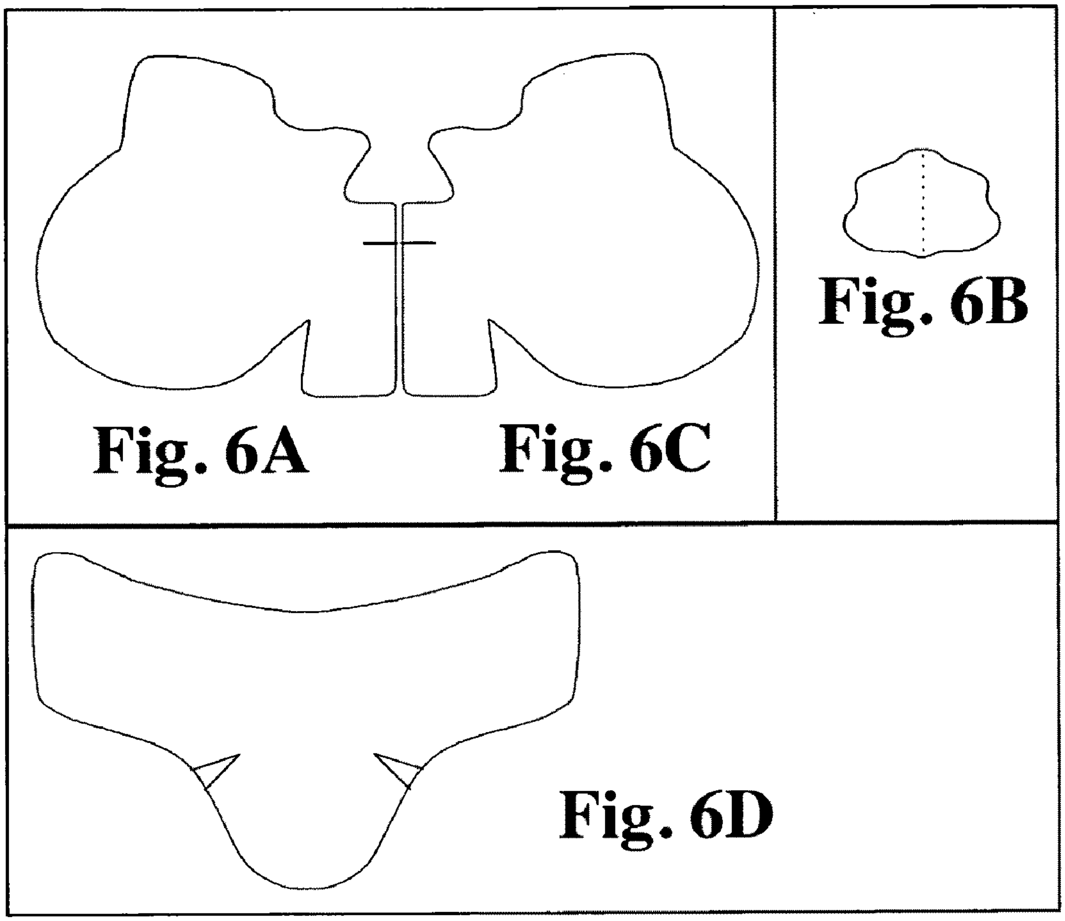
FIGS. 6A through 6I illustrate alternate applicators that apply a pattern to portions of a face, nose, and neck.
Figure 6B:
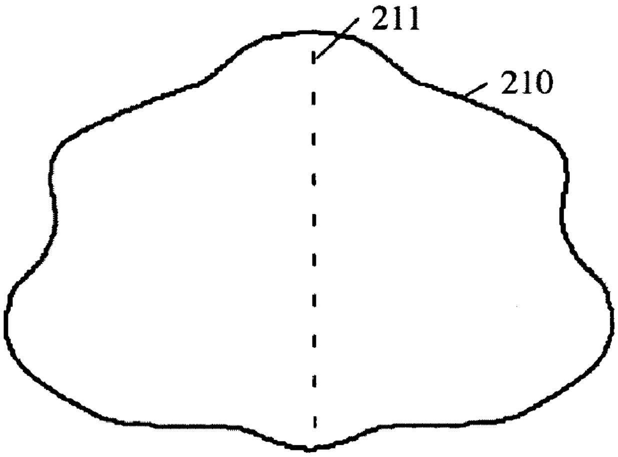

FIGS. 6A Through 6I—Skin Camouflage Applied to the Portions of the Face and Neck FIG. 6 shows another embodiment of an applicator set 800, further shown in FIG. 6A through 6D. FIGS. 6A through 6D illustrate alternate applicators that apply a pattern to portions of a face, nose, and neck. In this embodiment of the invention, the user 100 is wearing a hat with a brim, and does not need to have his forehead camouflaged. For improved ease of application, an applicator is provided for each half of the remaining face, i.e. first half-face applicator 600 (FIG. 6A), and second half-face applicator 602 (FIG. 6B). Each half-face applicator has a half nose cutout (606*a* and 606*b*, respectively), a half mouth cutout (608*a* and 608*b*, respectively), and a chin dart (612 and 614, respectively).

FIG. 6B illustrates a nose applicator 210 (FIG. 2B). FIG. 6G illustrates an alternate, wide nose applicator 250 which is easier to apply resulting in smoother application across the contours of the nose and cheeks. Each contains a nose fold 211 down the center.

FIG. 6 also shows a neck applicator 620 (FIG. 6D), which wraps around the neck 114 and covers a portion of the upper chest most like to be uncovered by most shirts and jackets 550, and most susceptible to sunburn. Darts (not shown) allow the neck applicator 620 to better form to the 3-dimensional neck 114 and upper chest.

Figure 6I:
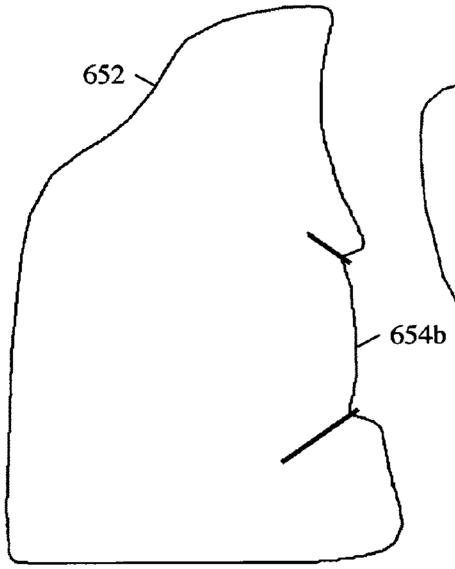
Figure 6C:
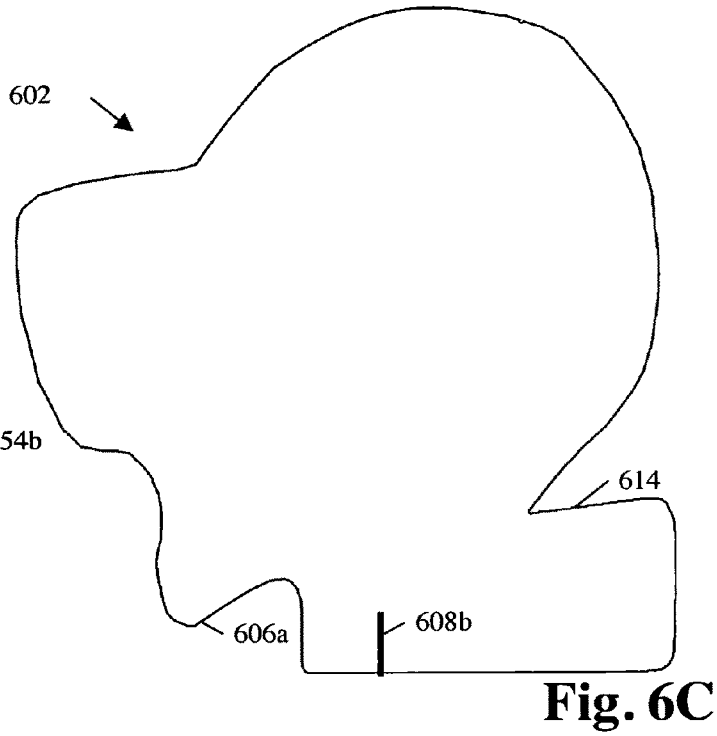
Figure 6H:
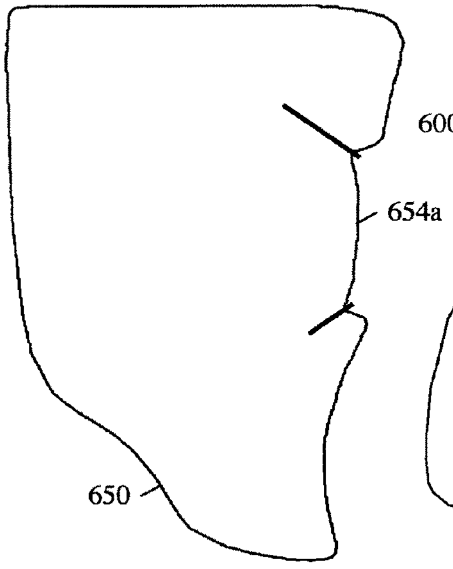
Figure 6A:
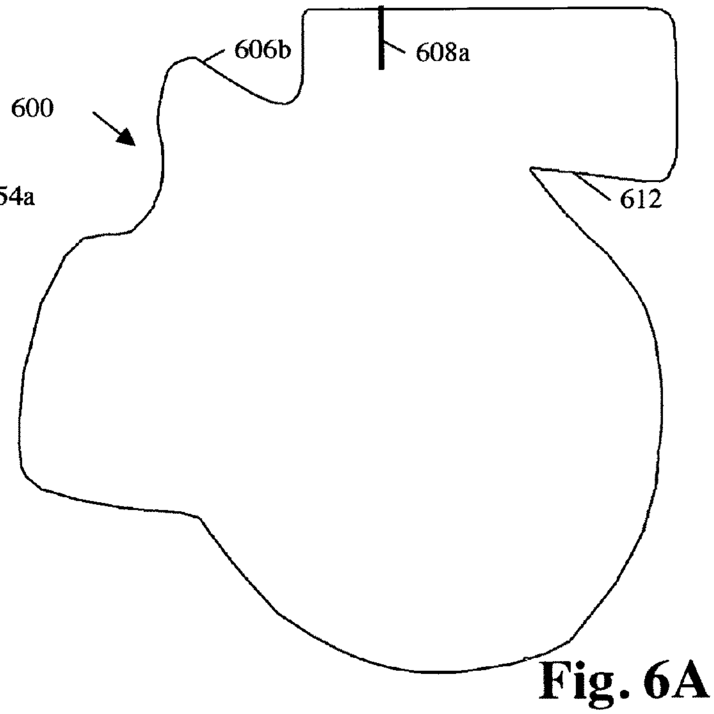
Figure 6D:
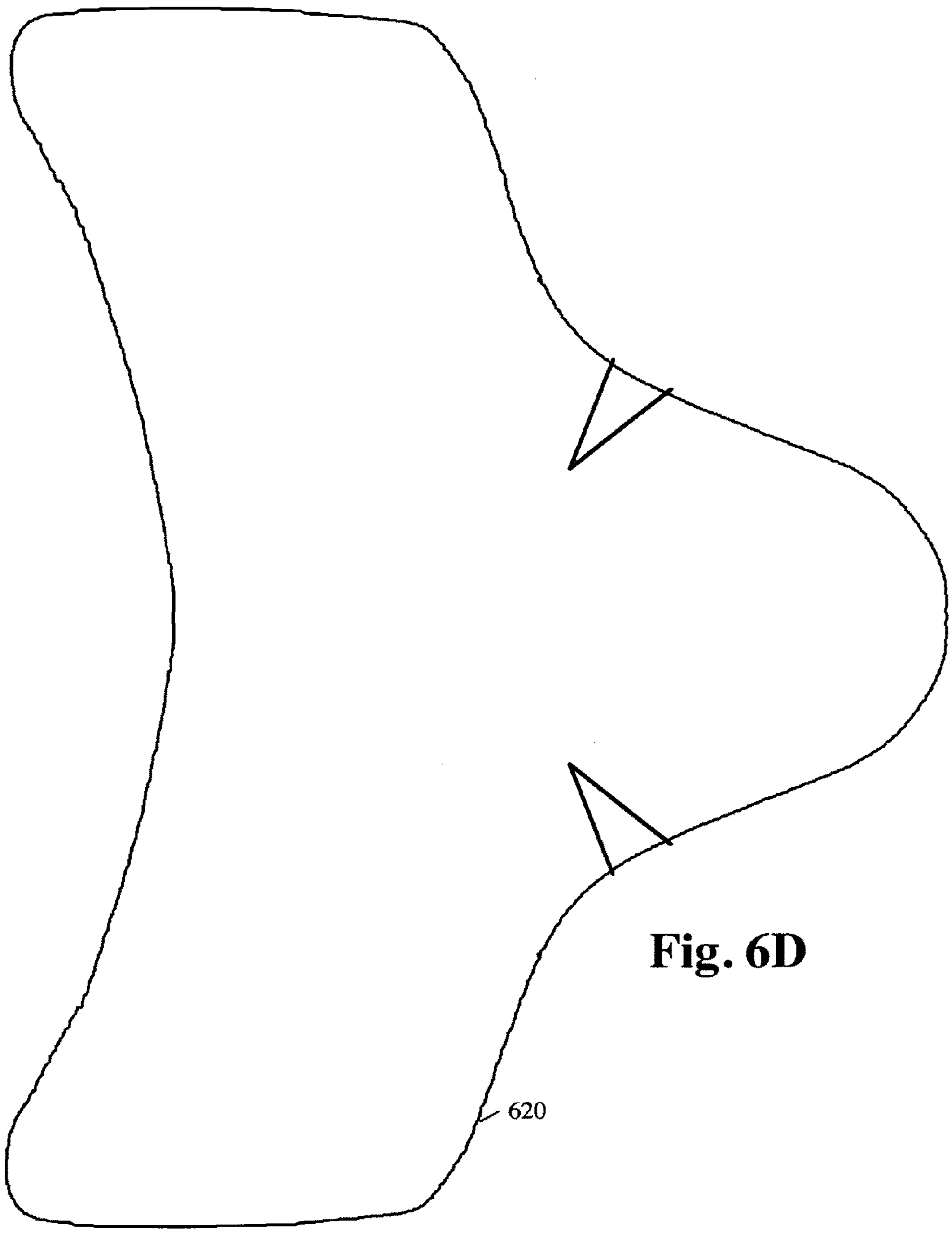

FIG. 6H and FIG. 6I illustrate the first half-brow applicator 650 and the second half-brow applicator 652 respectively, each containing an eyelid cutout 654(*a-b*) respectively. While not shown in FIG. 6, these two applicators can be used in conjunction with the first half-face applicator 600 (FIG. 6A) and second half-face applicator 602 (FIG. 6B) when the user 100 is not wearing a hat with a brim and requires his forehead camouflaged (see FIG. 7).

Incorporating Facial Hair

Figure 6F:
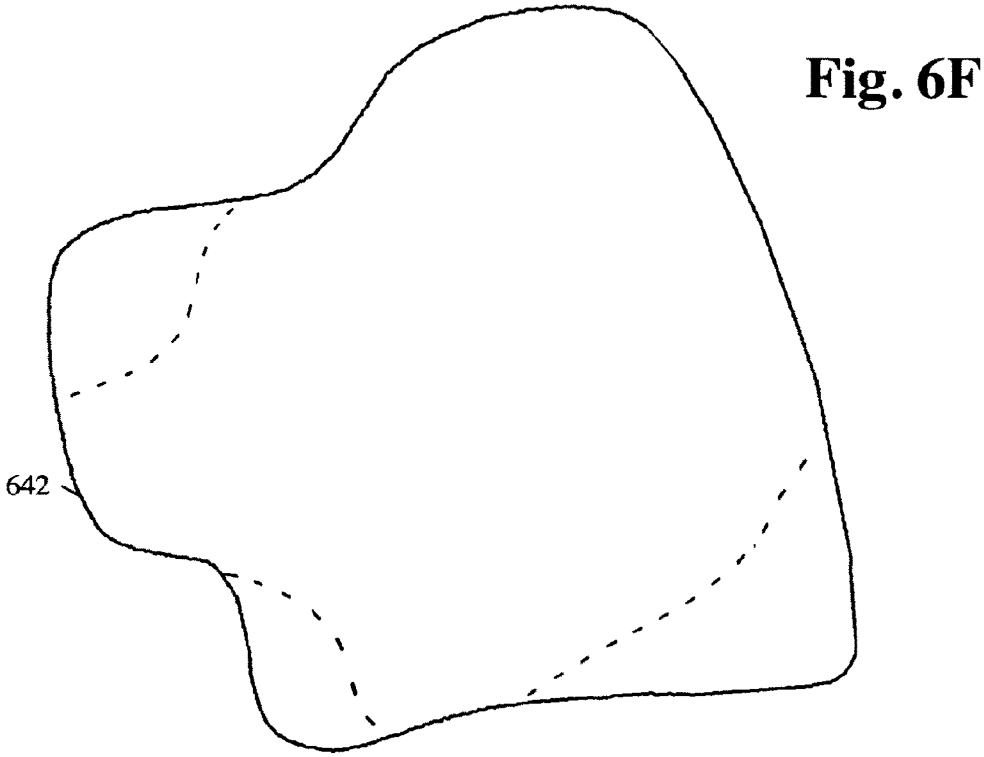
Figure 6E:
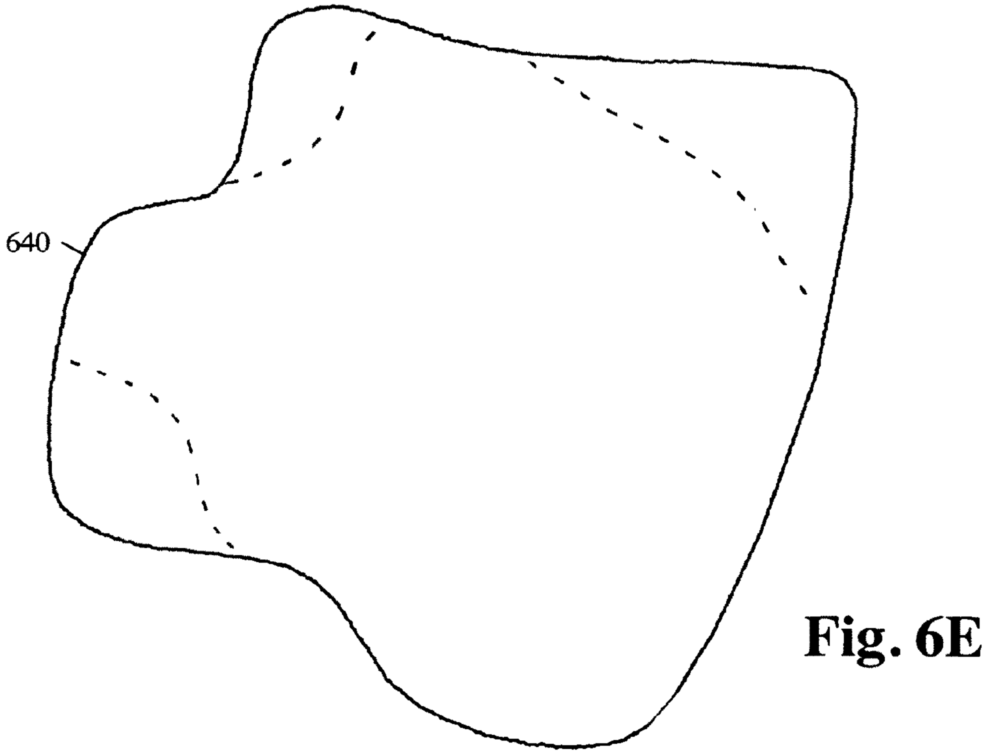
Figure 6G:
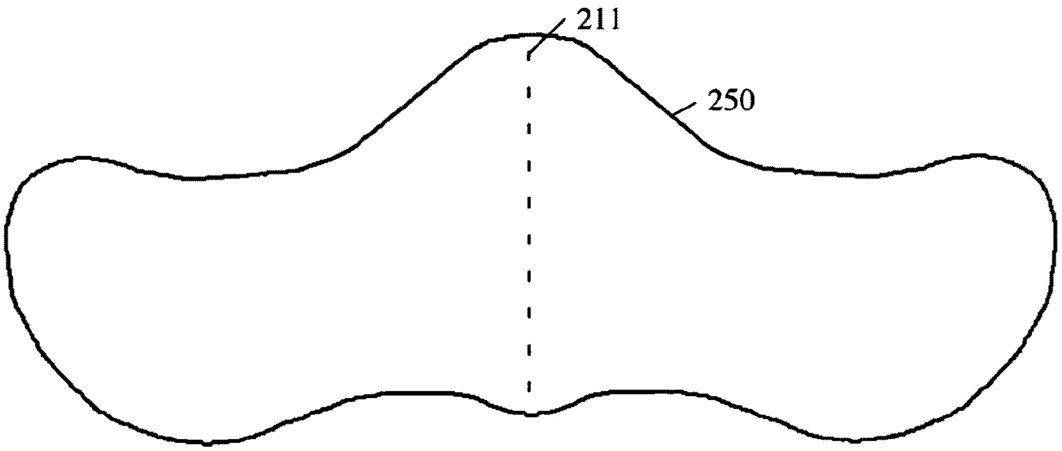

FIGS. 6E and 6F illustrate applicators that apply a pattern to a face of a man with a beard and mustache. Similar to the half-face applicators (FIGS. 6A and 6C), alternate half-face applicators (640 or 642) have cutouts allowing the user to place the camouflage around an existing beard or mustache. The user could create these shapes by cutting down the half-face applicators of FIGS. 6A and 6C, or these applicators could be additional sheets in the applicator set (allowing the user to choose the ones that best meet his personal needs).

If desired, the user could apply pigment over facial hair.

Figure 7:
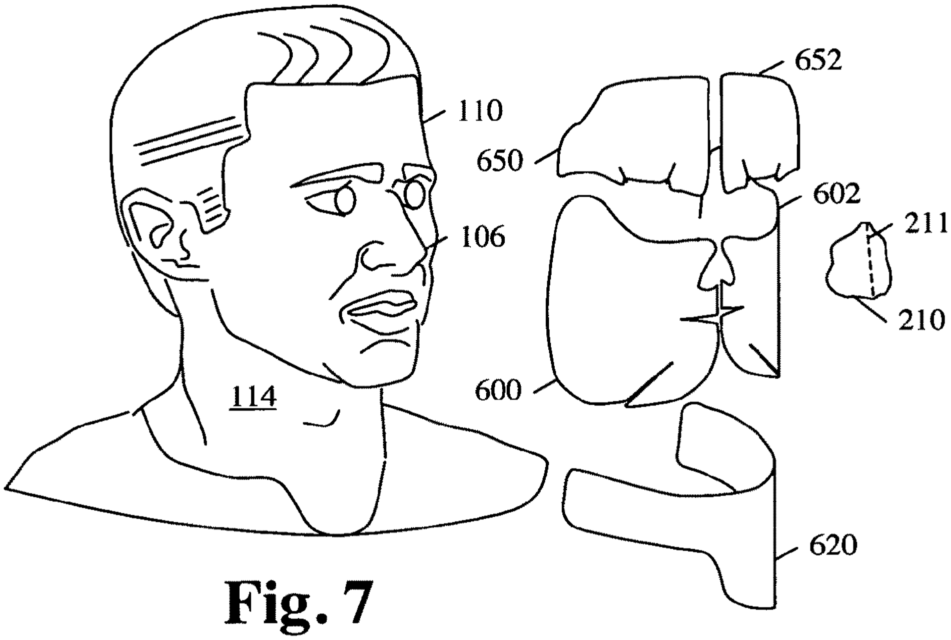
FIG. 7 illustrates shows the application a pattern to portions of a face, nose, and neck.

FIG. 7—Skin Camouflage Applied to Portions of the Face and Neck

FIG. 7 illustrates the application of a pattern to portions of a face 110, nose 106, and neck 114. The nose applicator 210 applies the desired pattern to the nose 106. The nose fold 211 should be centered on the nose 106. The half-face applicators (600, 602) apply the desired pattern to respective portions of the face 110. The half-brow applicators (650 or 652) apply the desired pattern to respective portions of the face 110. The neck applicator 620 applies the desired pattern to the neck 114 and upper chest.

Figure 8A:
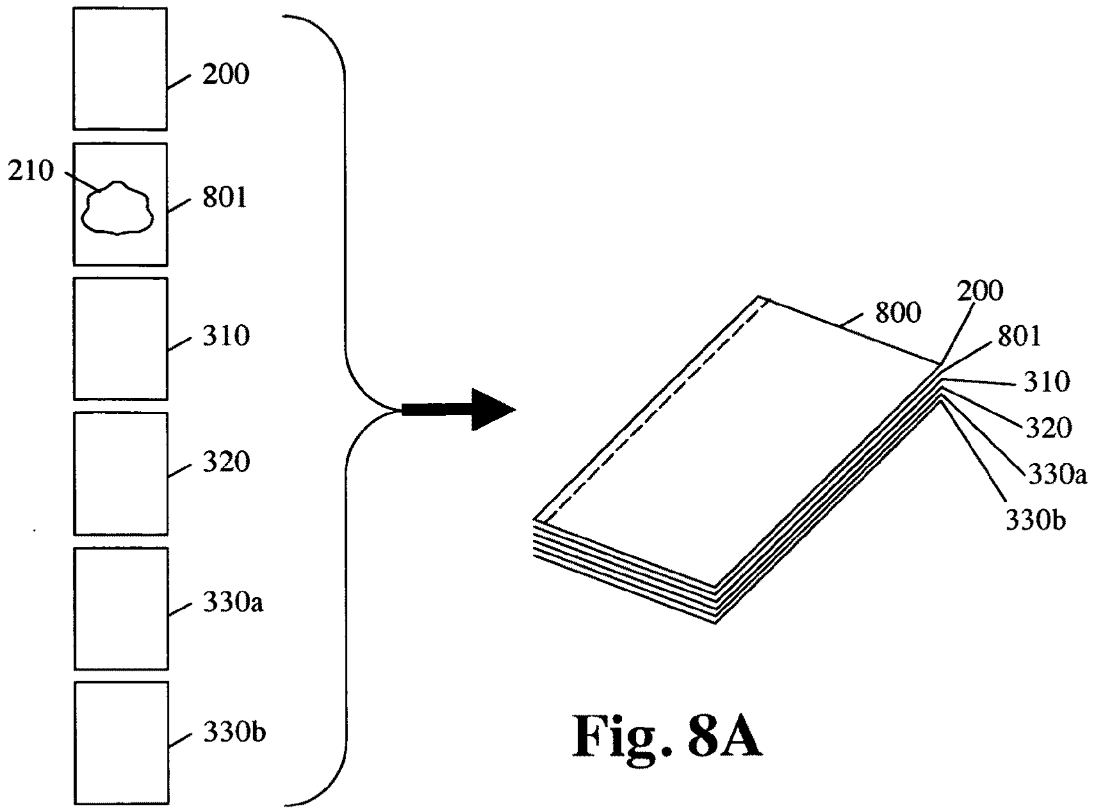
FIGS. 8A and 8B illustrate groups of applicators forming a set and a book consisting of multiple applicator sets.
Figure 8B:
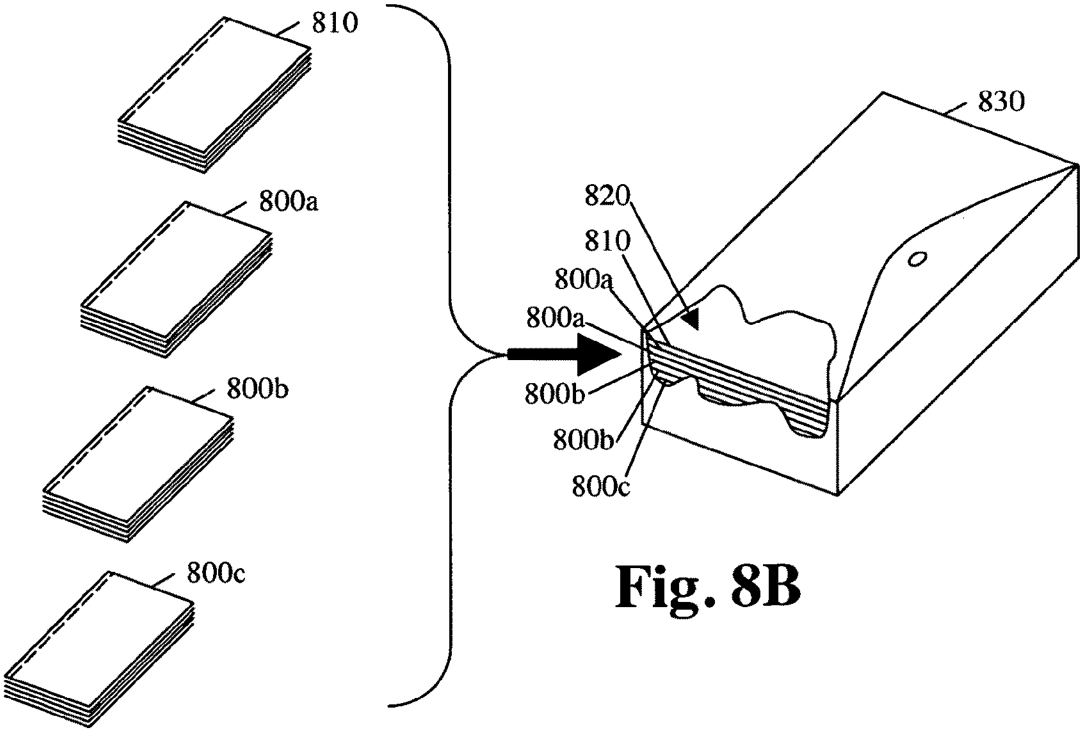

FIGS. 8A and 8B—Pattern Sets and Books of Sets

FIGS. 8A and 8B illustrate groups of applicators forming a set and a book consisting of multiple applicator sets.

FIG. 8A shows an exemplary applicator set 800 comprising a face applicator 200, nose page 801 having a nose applicator 210, a hand applicator 310, a forearm applicator 320, and both sheets of an upper-arm applicator 330 (330*a* and 330*b*, respectively).

FIG. 8B shows a book 820 comprising front matter 810 and multiple applicator sets (800*a*, 800*b*, 800*c*, for example). The book could have multiple copies of the same applicator set (as shown, for example, by two instances of 800*a*, and two instances of 800*b*) or could have multiple applicator sets 800 (each with a different pattern, e.g. one of 800*a*, one of 800*b*, one of 800*c*, and so forth). The book 10 is shown in a book container 830. The book container could be a three ring binder, a water proof bag, a binder with a locking zipper seal, or a box with a snap closure.

Figure 9A:
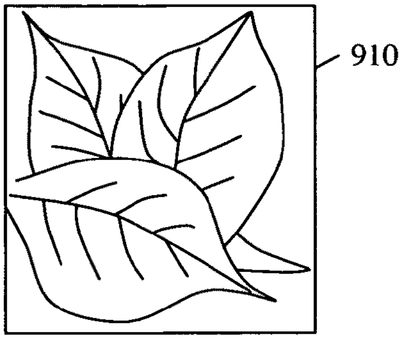
FIGS. 9A through 9C illustrate application of a matching pattern by using a plurality of applicators having different elements of the pattern to be matched.
Figure 9B:
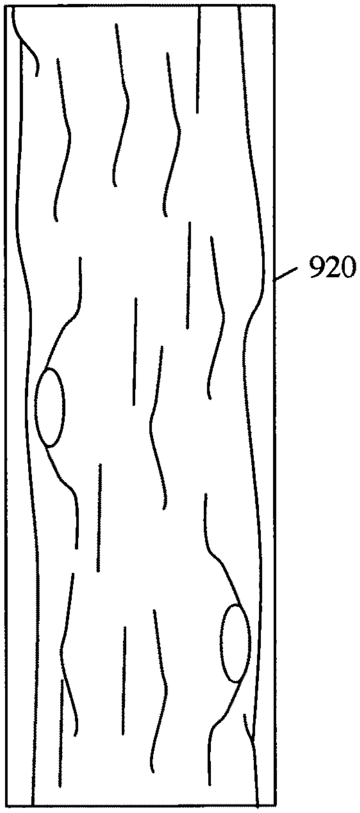
Figure 9C:
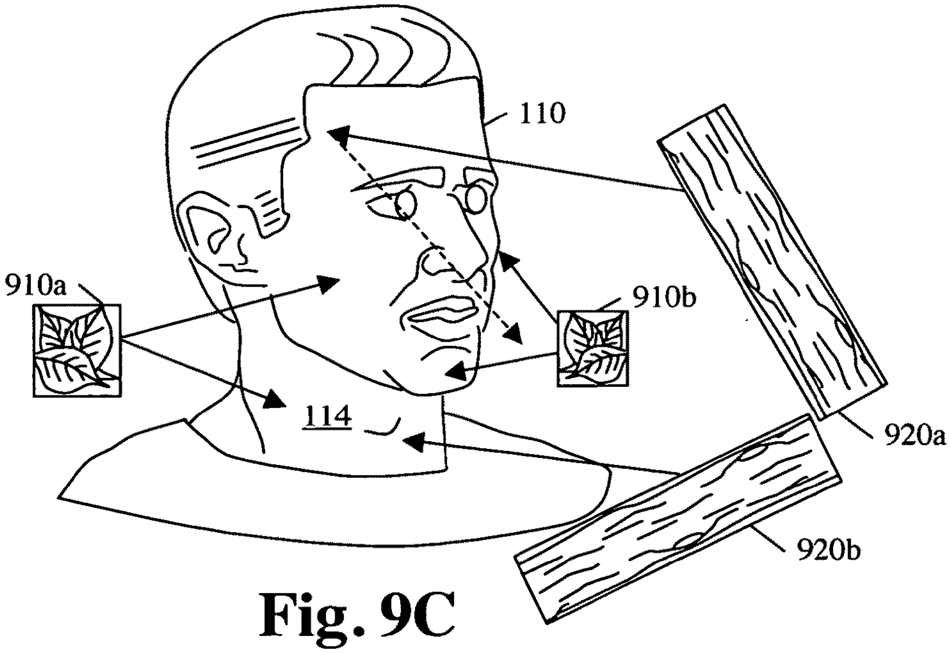

FIGS. 9A and 9C—Multiple Pattern Elements

FIGS. 9A through 9C illustrate application of a matching pattern by using a plurality of applicators having different elements of the pattern to be matched.

In this embodiment, the camouflage pattern is comprised of different elements, for example, green leaves, golden brown leaves, light branches, dark branches, brush, and so forth. Each of the elements is provided as separate applicators.

FIG. 9A shows an exemplary leaf element 910. FIG. 9B shows an exemplary branch element 920. FIG. 9C shows a user applying different branches 920*a*, across his face 110, and 920*b*, around his neck 114. Next, different leaf elements (910*a* and 910*b*) are applied. In this aspect of the invention, the user is able to place multiple elements to better match his apparel or create a custom layout using a combination of applicators to effectively camouflage the face.

This invention anticipates that effect camouflage can be created without covering every square inch of skin, but by breaking up the lighter colors of the face with darker strips or elements.

Figure 9D:
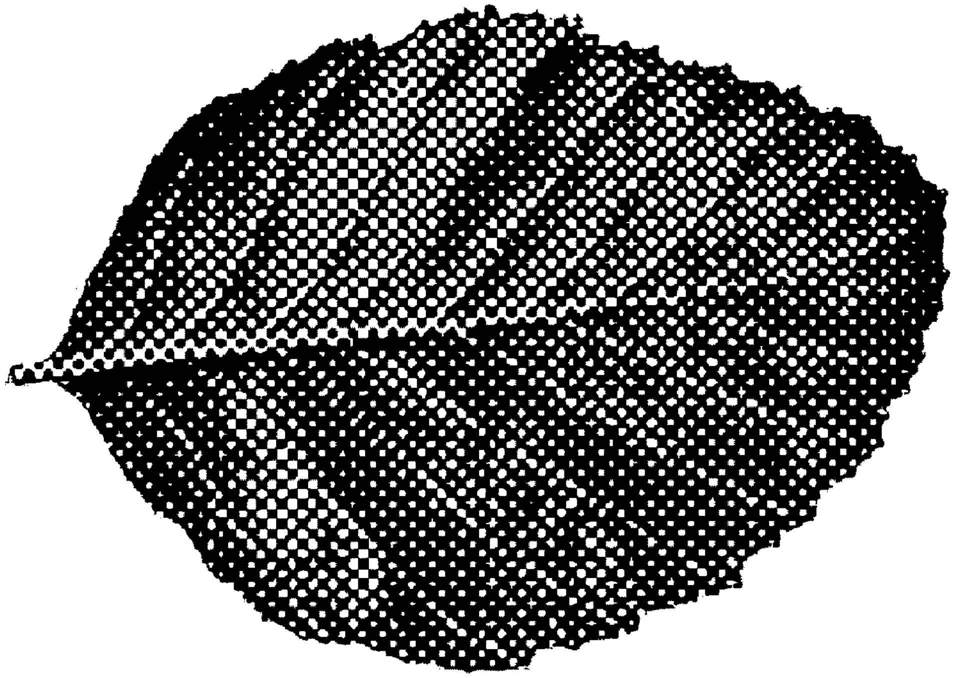
FIGS. 9D through 9G illustrate examples of alternate pattern elements.
Figure 9E:
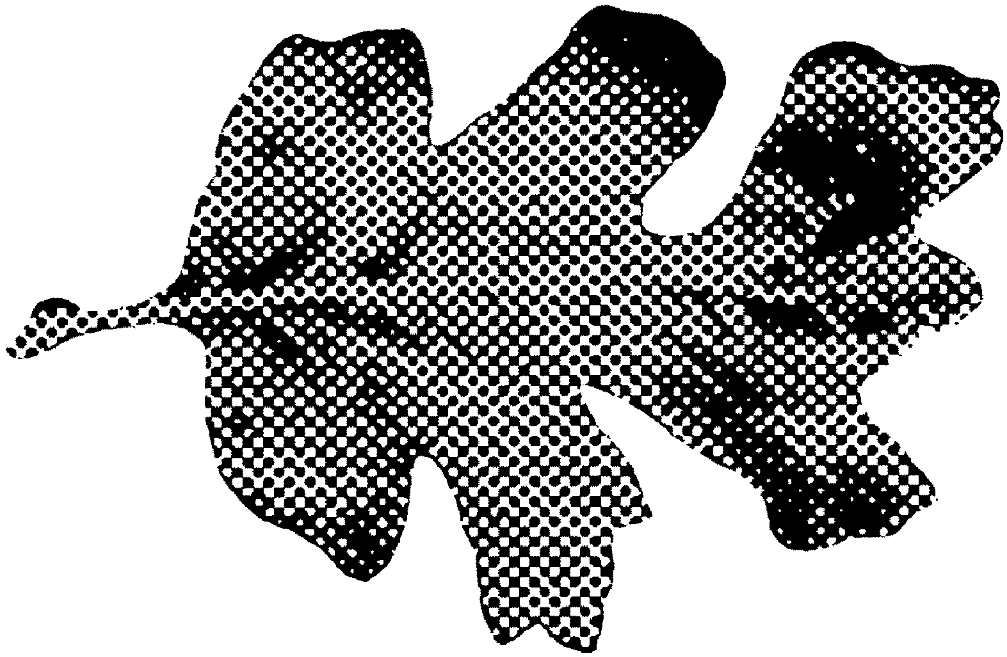
Figure 9F:
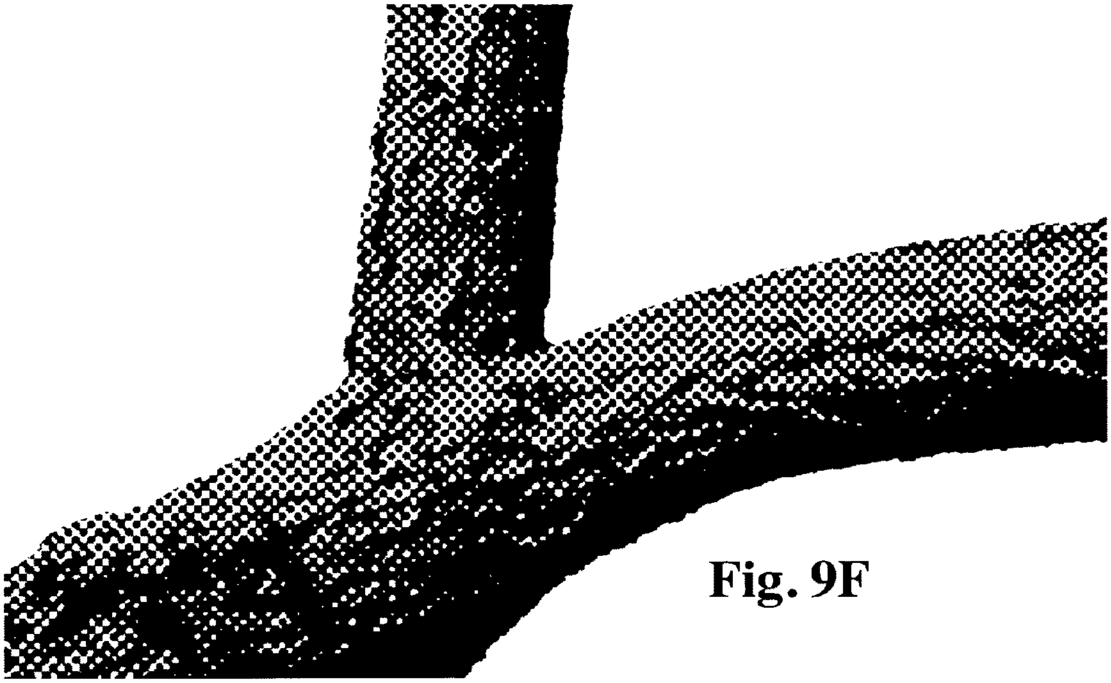
Figure 9G:
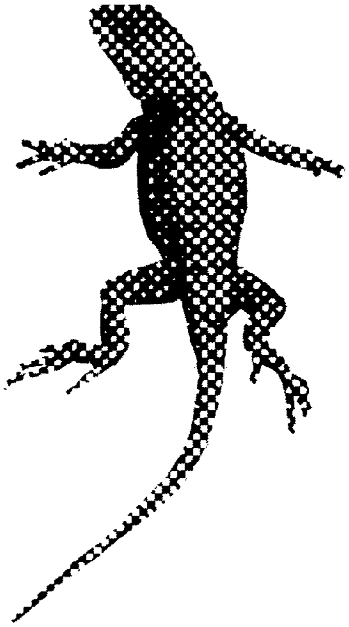

FIGS. 9D and 9G—Additional Pattern Elements

FIGS. 9D through 9G illustrate examples of additional pattern elements. FIGS. 9D and 9E illustrate leaves. FIG. 9F illustrates tree branches. FIG. 9G illustrates a lizard.

FIGS. 10A Through 10F—Structural Views of Wet and Dry Applicators

FIGS. 10A through 10F illustrate structural views of wet and dry applicators. Each view describes the layers that comprise the structure of an applicator.

Figure 10A:
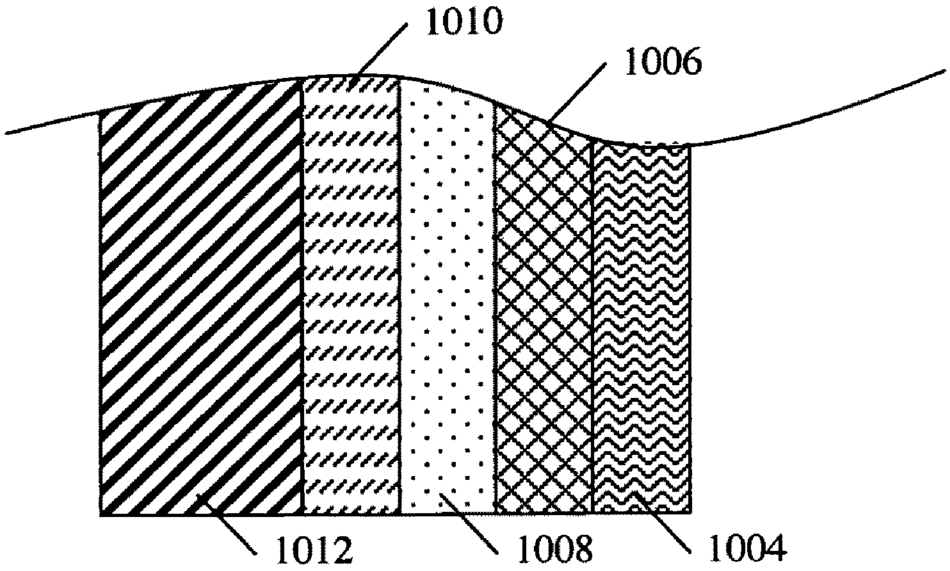
FIGS. 10A through 10F illustrate structural views of wet and dry applicators.

FIG. 10A illustrates a dry applicator comprising, in sequence, dry release layer 1004, film layer 1006, pigment layer 1008, adhesive layer 1010, and a peel off layer 1012. The dry release layer 1004 comprises backing paper or film that provides a foundation for the manufacturing process and protects the other layers during packaging, distribution, and application. The dry release layer 1004 is removed after the pigment is applied. The film layer 1006 is typically relatively thin and transparent and is the receiving layer for the pigment during the manufacturing process. After the pigment is applied to the skin, film layer 1006 becomes the outer layer and protects the pigment from easily rubbing off. The pigment layer 1008 is printed onto the film during the manufacturing process. The adhesive layer 1010 is applied directly to the skin and holds the pigment in place after the peel off layer 1012 is removed. Preferably, the adhesive is a medical adhesive which has be cleared by the FDA for long term application to human skin. Preferably, the film layer 1006, pigment layer 1008, and the adhesive layer 1010 are porous after application to the skin allowing the skin to breath and allowing sweat to pass through and evaporate.

A dry applicator is used by optionally cutting the applicator to the desired size and shape; removing the peel off layer 1012, applying the remaining layers with the adhesive layer 1010 toward the skin, pressing the remaining layers against the skin, and then removing the dry release layer 1004.

Figure 10B:
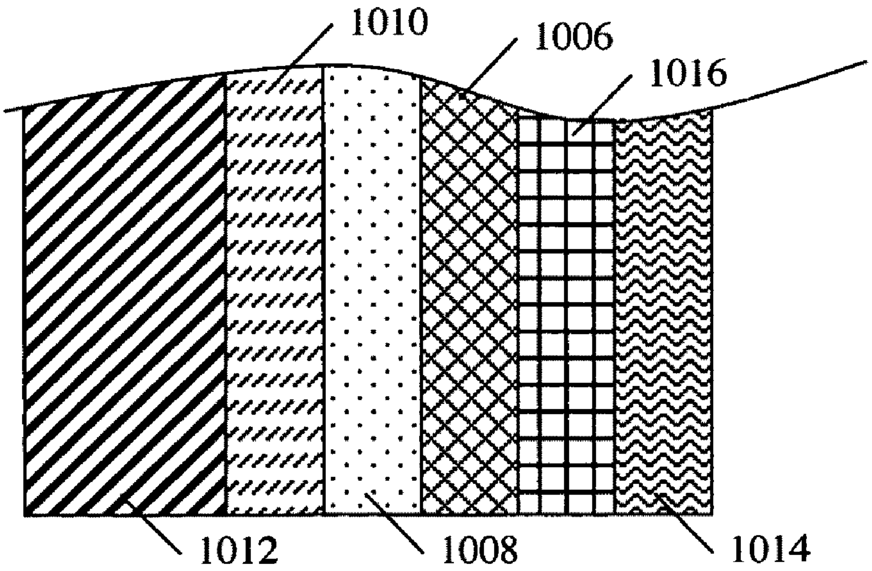

FIG. 10B illustrates a wet applicator comprising, in sequence, wet release layer 1014, solute layer 1016, film layer 1006, pigment layer 1008, adhesive layer 1010, and a peel off layer 1012. Manufacturing and use of wet applicator is similar to the dry applicator. The wet release layer 1014 backing paper or film that provides a foundation for the manufacturing process and protects the other layers during packaging, distribution, and application. The wet release layer 1014 is coated with a solute layer 1016 (which is a sizing agent) and which dissolves when the applicator is wet with a solvent (which typically is water). The wet release layer 1014 is removed after the pigment is applied by dissolving the solute layer 1016. The film layer 1006 is typically relatively thin and transparent and is the receiving layer for the pigment during the manufacturing process. After the pigment is applied to the skin, film layer 1006 becomes the outer layer and protects the pigment from easily rubbing off. The pigment layer 1008 is printed onto the film during the manufacturing process. The adhesive layer 1010 is applied directly to the skin and holds the pigment in place after the peel off layer 1012 is removed. Preferably, the adhesive is a medical adhesive which has been cleared by the FDA for long-term application to human skin. Preferably, the film layer 1006, pigment layer 1008, and the adhesive layer 1010 are porous after application to the skin allowing the skin to breath and allowing sweat to pass through and evaporate.

A wet applicator is used by optionally cutting the applicator to the desired size and shape; removing the peel off layer 1012, applying the remaining layers with the adhesive layer 1010 toward the skin, pressing the remaining layers against the skin, and then removing the wet release layer 1014 by dissolving the solute layer 1016 with water.

Figure 10C:
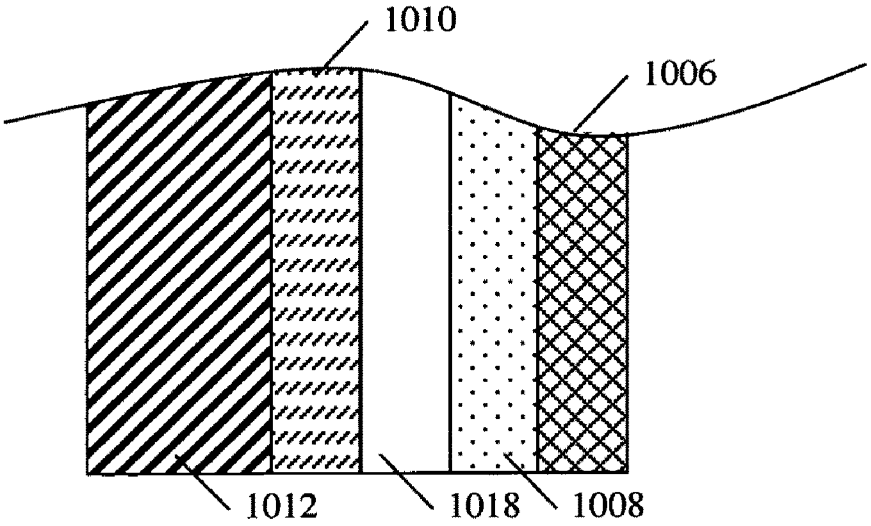

FIG. 10C illustrates an alternate applicator comprising, in sequence, film layer 1006, pigment layer 1008, opaque layer 1018, adhesive layer 1010, and a peel off layer 1012. In practice, with some printing methods, the pigment layer is thin and allows the color of the skin to show through. For some situations where the true color of the predetermined pigment pattern is desired, regardless of skin color, the opaque layer 1018 preserves the desired appearance of the pigment. The opaque layer could be an extra layer of white pigment or could be a predominate base color, for example the base color of a three or four color military camouflage pattern.

Figure 10D:
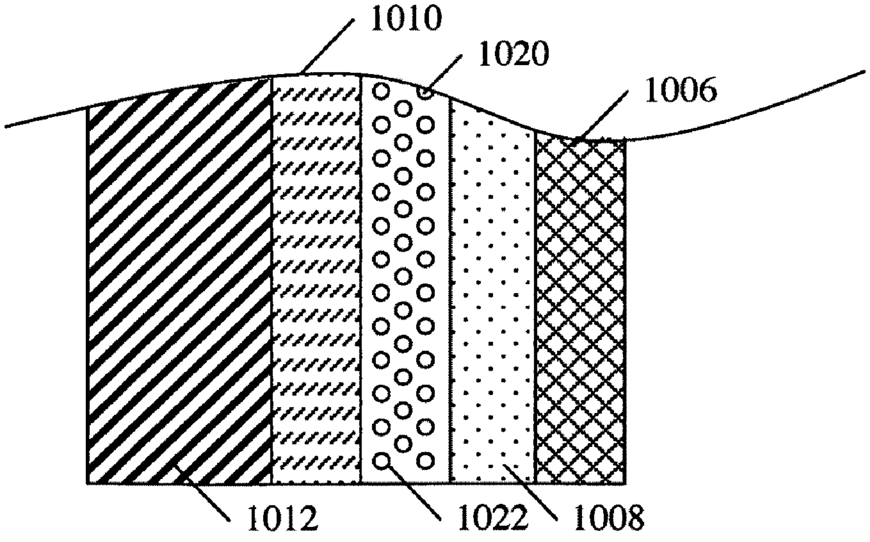

FIG. 10D illustrates an extreme heat resistant applicator comprising, in sequence, film layer 1006, pigment layer 1008, heat shield layer 1020, adhesive layer 1010, and peel off layer 1012. The heat shield layer 1020 comprises of heat reflective and insulating particles similar to the ceramic used to make the Space Shuttle heat shield tiles. Relatively small ceramic bubbles 1022 are commercially available as a white powder which can mixed into paint to provide heat resistance. Our novel extreme heat resistant applicator combines heat reflective particles, such as the ceramic bubbles 1022, with the other layers. The ceramic bubbles 1022 in the heat shield layer 1020 provide heat resistant characteristics and allows the heat shield layer to also serve as an alternative form of the opaque layer 1018.

Figure 10E:
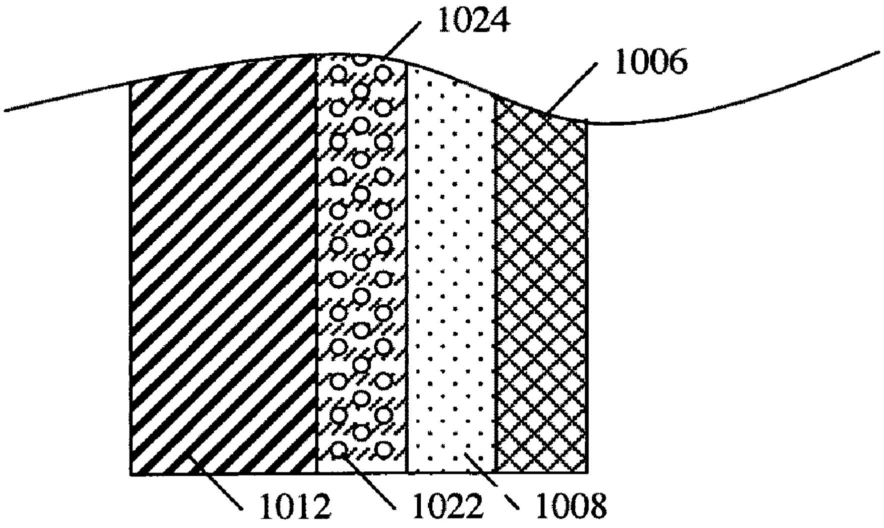

FIG. 10E illustrates an alternate heat resistant applicator comprising, in sequence, film layer 1006, pigment layer 1008, adhesive/heat shield layer 1024, and a peel off layer 1012. In this embodiment, the adhesive layer 1010 entrains ceramic bubbles 1022 in the adhesive to provide heat resistant characteristics allowing for a thicker layer.

Figure 10F:
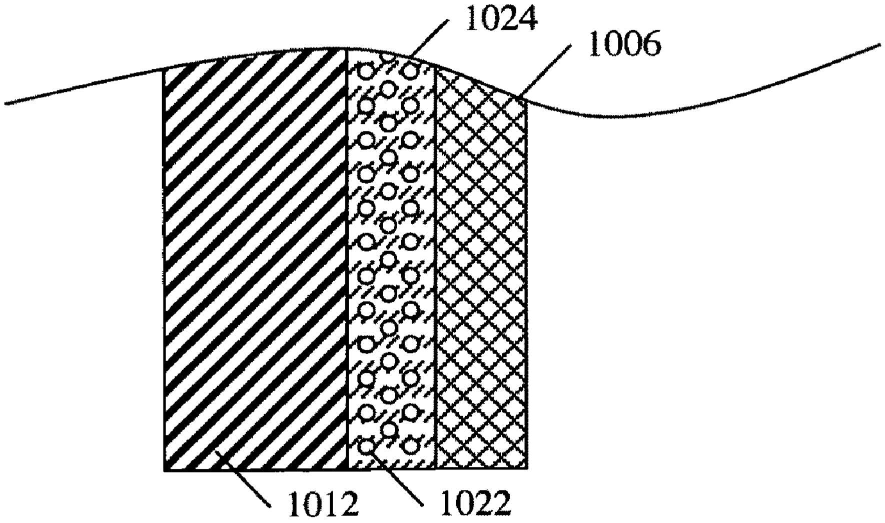

FIG. 10F illustrates an pigment free heat resistant applicator comprising, in sequence, film layer 1006, adhesive/heat shield layer 1024, and a peel off layer 1012. As in FIG. 10E, the adhesive/heat shield layer 1024 combines ceramic bubbles 1022 with the adhesive to provide heat resistant characteristics. This is ideal for anyone requiring heat resistance without the need for camouflage, such as firefighters, metal workers, glassblowers, or cooks.

Other Uses

While the descriptions of the various embodiments have been made in reference to hunting and military uses, the present invention could also be used for other activities such as makeup for stage and video actors, costume wearers, sport fanatics, or groups of people who want a uniform appearance.

In the example of a long running stage production, multiple predetermined patterns are applied to multiple actors each day, each pattern could be embodied in a set of applicators and mass produced. Use the methods disclosed above, the pattern could be applied to each respective actor and touched up as needed with makeup. This would significantly reduce the time and cost associated with applying the daily stage makeup. The mass produced applicators could be licensed to traveling versions of the show, local theater groups, and high schools along with the scripts and scores.

In the example of a feature film, video is shot over a period of many days or months; however it is important the appearance of the actors have continuity. For example, if a character is cut in a fight, a scar needs to appear in the same place in all the scenes that appear after the fight chronologically, and should not appear in any scenes that appear before the fight. However, because of different set locations and the use of sound stages, scenes are not shot on the same day and are not shot in chronological order. Some scenes require multiple days of shooting video from different angles. This invention can be used to create predetermined patterns which are applied to multiple actors each day. This would significantly reduce the time and cost associated with applying the daily film makeup and would insure continuity of the precise features, e.g. of a scar, and placement, e.g. the same place.

In the example of costume wearers, there is a large market for certain Halloween, Marti Gras, Carnival, or other costumes. For example, Captain Jack Sparrow from Disney's Pirates of the Caribbean is a very popular Halloween costume. A design having the Captain Jack's entire face could be mass produced and sold along with beard, jewelry, and clothing.

In the example of sport fanatics, conventionally some fans paint their face or chest and may apply small decals with the sports logo. With one aspect of the current invention, a precise, high quality team logo could be applied across the entire face, or across the chests of a series of fans with high quality letters and accurate colors.

In the examples of groups of people who want a uniform appearance, people in a protest could all have a flag of a suppressed group applied to their faces; people in a St. Patrick's Day parade could have shamrocks on their faces; people walking to raise money for a cause could each have a pink ribbon on their face and arms and continuing on a t-shirt.

In the example, of a camouflage pattern licensor, top professional hunters and tradeshow models could be dressed apparel in the latest pattern with any uncovered skin continuously applied with the same, matching pattern. The professional hunters could stand in front of a wall or blind made in the same pattern. The models could have a large percentage of their body covered in skin camouflage prepared specifically for the tradeshow demonstration impact. The models could walk around the tradeshow floor or work in the both. Complimentary applicators could be given away as promotional items.

In the case where a military unit is involved in an activity for a specific period of time, every member of the unit could be given a particular set of applicators, so that members of the unit can recognize each other by unique features of the pattern. The pattern could be switched at certain times.

Variety of Applicators

The applicators of the present invention could be implemented in with various processes. For some use the conventional water release decal-type temporary tattoo could be used to apply the pigment. For other uses the new waterless temporary tattoo would be preferred. Other devices and processes are also anticipated. For example, the predetermined pattern of pigment could be infused into a plastic film or substrate that could be used to repeatedly apply the pigment (similar to a self inking stamp).

Advantages

Simple

The present invention is simple to make and use. The present invention significantly reduces the time to put on.

Easy to Use

The present invention is easy to use.

Comfortable

Unlike conventional method of face and hand concealment, the present invention is comfortable to wear, and can be worn for long periods of times.

Breathable

The present invention allows the skin to breath.

Effective

The applicators and methods of the present invention are effective.

Efficient

The use of the present invention is efficient. A predetermined pattern can be quickly applied with high quality appearance and effect.

Quality and Precision

The applicators and methods of the present invention result in a high quality, precisely detailed and placed pattern of pigment that is not achieved with conventional face paint or makeup kits.

Marketing

The present invention is highly marketable as products for field use and also has exciting implications for tradeshows and promotions.

Safe

Because of the vision and movement of the user is not blocked or disturbed by this means of face or hand concealment, the user will be safer. The hunter will be less likely to trip and fall, or get branches or equipment caught. The child in a Halloween costume will be safer (and more comfortable) that wearing traditional masks that can obscure vision.

The pigments or adhesives used are cleared by the FDA and comply with FDA regulations.

Quiet

The present invention allows a hunter or soldier to move through the brush more quietly by avoiding stepping on branches or leaves, and by reducing snags on branches.

Quick

The present invention can be quickly applied and removed.

Clean

Unlike the greasy mess and damage cause by conventional face paint or makeup, the present invention is relatively clean.

Unlike face paint or makeup, the invention has relatively little odor or scent.

Better Appearance

Conventional methods result in an inconsistent, less pleasing appearance.

Cost Effective

Because the applicators, sets, and books can be made relatively inexpensively, the present invention is cost effective. They can be applied by the user, without having to have an "artist" take the time to create the pattern upon each application.

Long Storage Period

The applicators of the present invention are easy to store and should have a long shelf life.

Sunburn Protection

The pigment and transfer substrate can provide long lasting (multi-day) sunburn protection for the uncovered skin of the user.

Extreme Heat Protection

The ceramic bubbles can provide heat protection for the uncovered skin of the user.

CONCLUSION, RAMIFICATION, AND SCOPE

Accordingly, the present invention provides an easy to use, simple, safe, comfortable, efficient, and effective means for concealing the face or hands of a user.

While the above descriptions contain several specifics these should not be construed as limitations on the scope of the invention, but rather as examples of some of the preferred embodiments thereof. Many other variations are possible. For example, the pattern can be broken up and applied by applicators or various sizes and shapes. Additionally, the applicators could be made of different materials or have additional features, or be used in different activities, without departing from the scope and spirit of the novel features of the present invention.

Accordingly, the scope of the invention should be determined not by the illustrated embodiments, but by the appended claims and their legal equivalents.

We claim:

1. An applicator for applying a heat shield on skin of a human body part, the applicator comprising:

a) a pigment layer having a predetermined pattern of pigment,
 whereby the skin is concealed, b) a heat shield layer, c) a skin attachment layer for holding the heat shield layer on the skin, wherein the predetermined pattern of pigment is a high resolution image having at least 100 pixels per inch, wherein the heat shield layer protects the skin from extreme heat, and wherein the applicator has a predetermined shape corresponding to the body part, whereby the applicator is used to apply the heat shield to the body part, and whereby the skin of the body part is protected.

2. The applicator of claim 1 wherein the skin attachment layer is an adhesive layer.

3. The applicator of claim 1 heat shield layer comprises heat reflective particles.

4. The applicator of claim 1 heat shield layer comprises insulating particles.

5. The applicator of claim 1 heat shield layer comprises ceramic bubbles having a spherical shape and filled with insulating gas.

6. The applicator of claim 1 wherein the heat shield layer comprises an opaque layer under the pigment layer, whereby the apparent color of the pigment is the same when applied to different skin colors.

7. The applicator of claim 2 further comprising a peel off layer.

8. The applicator of claim 2 further comprising a dry release layer.

9. The applicator of claim 2 further comprising a solute layer and a wet release layer.

10. The applicator of claim 1 wherein the corresponding body part is a hand.

11. The applicator of claim 1 wherein the corresponding body part is a face.

12. The applicator of claim 1 wherein the corresponding body part is an arm.

13. The applicator of claim 1 wherein the corresponding body part is one a group of an ear, a whole face, a forearm, an upper arm, a throat, and a brow.

14. The applicator of claim 1 wherein the applicator is divided into multiple pieces, whereby each piece is applied to different areas of the body part separately to form a single contiguous protective shield.

15. The applicator of claim 1 wherein the predetermined pattern of pigment is a military camouflage pattern.

16. A system comprising a plurality of applicators of claim 1 organized in a set, wherein each adapter in the set contains predetermined pattern of pigment taken from a larger camouflage pattern, wherein when applied to the skin, the larger camouflage pattern appears continuously over the respective body parts.

17. A method of applying the flexible heat shield of the applicator of claim 2 to the skin, the applicator having a protective backing layer, the method comprising the steps of:

a) attaching the adhesive layer to the skin of the predetermined body part, and b) removing the backing layer, wherein the heat shield provides protection to the skin, wherein the heat shield remains attached to the skin for a predetermined period of days.

18. A method of applying the flexible heat shield of the applicator of claim 7 to the skin, the method comprising the steps of:

a) peeling off the peel off layer, b) attaching the remaining layers to the skin of the predetermined body part, and wherein the heat shield provides protection to the skin, wherein the heat shield remains attached to the skin for a predetermined period of days.

19. The method of claim 17, wherein the predetermined pattern of pigment remains attached to the skin for the predetermined period of days.

20. The method of claim 18, wherein the predetermined pattern of pigment remains attached to the skin for the predetermined period of days.

* * * * *